(12) United States Patent
De Ridder

(10) Patent No.: US 8,897,870 B2
(45) Date of Patent: Nov. 25, 2014

(54) STIMULATION DESIGN FOR NEUROMODULATION

(71) Applicant: Advanced Neuromodulation Systems, Inc., Plano, TX (US)

(72) Inventor: Dirk De Ridder, Zelate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 13/846,663

(22) Filed: Mar. 18, 2013

(65) Prior Publication Data

US 2013/0231713 A1  Sep. 5, 2013

Related U.S. Application Data

(63) Continuation of application No. 13/314,966, filed on Dec. 8, 2011, now Pat. No. 8,401,655, which is a continuation of application No. 12/790,505, filed on May 28, 2010, now abandoned, which is a continuation of application No. 11/254,465, filed on Oct. 20, 2005, now Pat. No. 7,734,340.

(60) Provisional application No. 60/620,781, filed on Oct. 21, 2004.

(51) Int. Cl.
*A61N 1/36* (2006.01)
*A61N 1/05* (2006.01)
*A61N 2/00* (2006.01)
*A61M 5/142* (2006.01)

(52) U.S. Cl.
CPC ............. *A61N 1/3606* (2013.01); *A61N 2/006* (2013.01); *A61N 1/36085* (2013.01); *A61N 1/36032* (2013.01); *A61N 1/36021* (2013.01); *A61N 1/36096* (2013.01); *A61N 1/0531* (2013.01); *A61N 1/36017* (2013.01); *A61N 1/0553* (2013.01); *A61N 1/0529* (2013.01); *A61N 1/36117* (2013.01); *A61N 1/36071* (2013.01); *A61N 1/3611* (2013.01); *A61N 1/361* (2013.01); *A61M 5/14276* (2013.01)
USPC ............................................. 607/2

(58) Field of Classification Search
USPC ........................ 607/45–46, 55–57
See application file for complete search history.

(56) References Cited

U.S. PATENT DOCUMENTS

| | | | | |
|---|---|---|---|---|
| 6,466,822 B1 * | 10/2002 | Pless | ............................... | 607/45 |
| 6,529,774 B1 * | 3/2003 | Greene | ......................... | 600/545 |
| 6,671,555 B2 * | 12/2003 | Gielen et al. | .................... | 607/45 |
| 2006/0015153 A1 * | 1/2006 | Gliner et al. | .................... | 607/45 |

\* cited by examiner

Primary Examiner — Amanda Patton

(57) ABSTRACT

The present application relates to a new stimulation design which can be utilized to treat neurological conditions. The stimulation system produces a burst mode stimulation which alters the neuronal activity of the predetermined site, thereby treating the neurological condition or disorder. The burst stimulus comprises a plurality of groups of spike pulses having a maximum inter-spike interval of 100 milliseconds. The burst stimulus is separated by a substantially quiescent period of time between the plurality of groups of spike pulses. This inter-group interval may comprise a minimum of 5 seconds.

10 Claims, 4 Drawing Sheets

Regular Firing

Burst Firing

STIMULATION DESIGN FOR NEUROMODULATION

RELATED APPLICATIONS

This application is a continuation of U.S. application Ser. No. 13/314,966, filed Dec. 8, 2011, which is a continuation of U.S. application Ser. No. 12/790,505, filed May 28, 2010, pending, which is a continuation of U.S. application Ser. No. 11/254,465, filed Oct. 20, 2005, now U.S. Pat. No. 7,734,340, which claims the benefit of U.S. Provisional Application No. 60/620,781, filed Oct. 21, 2004, the disclosures of which are incorporated herein by reference in their entirety.

This application is also related to U.S. Provisional Application Nos. 60/620,762 filed, Oct. 21, 2004, 60/631,085 filed Nov. 24, 2004, 60/620,827 filed Oct. 21, 2004, 60/631,091 filed Nov. 24, 2004, 60/631,089 filed Nov. 24, 2004, 60/620, 847 filed Oct. 21, 2004, and 60/639,635, filed Dec. 27, 2004 each of which is incorporated by reference in its entirety.

TECHNICAL FIELD

The present application relates to a new stimulation system and method which can be utilized to treat neurological conditions and/or disorders.

BACKGROUND OF THE INVENTION

Different firing modes or frequencies occur in the brain and/or other neuronal tissue, for example tonic firing and burst firing (irregular or regular burst firing). Such firing modes can be utilized for normal processing of information, however, alteration of the firing modes, may also lead to pathology.

For example, certain neurological conditions are associated with hyperactivity of the brain and can be traced to a rhythmic burst firing or high frequency tonic firing (e.g., tinnitus, pain, and epilepsy). Other conditions can be associated with an arrhythmic burst firing or a desynchronized form of tonic and burst firing (e.g., movement disorders and hallucinations).

During the past decade, neuromodulation systems have been used to modulate various areas of the brain, spinal cord, or peripheral nerves (See, for example, U.S. Pat. Nos. 6,671, 555; 6,690,974). These types of systems utilize tonic forms of electrical stimulation. The disadvantage to these systems is that the neurological condition is related to a high frequency tonic rhythm or bursting type rhythm, it may be difficult for a second tonic stimulation to alter the diseased stimulation to actually result in treatment.

Thus, the present invention is the first to describe a neuromodulation design or stimulation parameters in which the stimulation parameters produce burst stimulation to override or alter the pathological and/or physiological stimulation to treat a neurological condition.

BRIEF SUMMARY OF THE INVENTION

The present invention is directed to a method and/or system of stimulating nerve tissue of a patient using an implantable pulse generator. The method comprises generating, by the implantable pulse generator, a burst stimulus that comprises a plurality of groups of spike pulses, wherein the burst stimulus is substantially quiescent between the plurality of groups, wherein each spike within each group is separated by a maximum inter-spike interval and each group of spikes is separated by a minimum inter-group interval, wherein the maximum inter-spike interval is 100 milliseconds and the minimum inter-group interval is 5 seconds; providing the burst stimulus from the implantable pulse generator to a medical lead; and applying the burst stimulus to nerve tissue of the patient via one or several electrodes of the medical lead. More particularly, each spike in each group occurs from a plateau potential, which is controllable by a parameter stored in the implantable pulse generator.

In certain embodiments, the method of stimulating nerve tissue comprises controlling a number of spikes within a group of spikes of the burst stimulus according to a parameter stored in the implantable pulse generator. The pulse generator is also capable of controlling a spike amplitude according to a parameter stored in the implantable pulse generator. In certain embodiments, the method comprises an amplitude of the hyperpolarizing pulse is controllable by a parameter stored in the implantable pulse generator.

Yet further, the method of stimulating nerve tissue comprises controlling an inter-spike interval according to a parameter stored in the implantable pulse generator and/or controlling an inter-group interval according to a parameter stored in the implantable pulse generator and/or controlling a number of groups within the burst stimulus according to a parameter stored in the implantable pulse generator.

In another embodiment, the method further comprises detecting, by the implantable pulse generator, hyperactivity within neural tissue using a sensor in the implantable pulse generator, wherein the generating the burst stimulus occurs in response to the detecting. The sensor is coupled to one or several electrodes of the medical lead.

The present invention is directed to a method and a system of neuromodulation by providing a burst mode stimulus to either central or peripheral neuronal tissue in which the burst mode stimulus alters the activity of the neuronal tissue. It is envisioned that this method of neuromodulation can be used to treat various neurological disorders or neurologically mediated disorders. Stimulation can be in the form of electrical and/or chemical stimulation. In certain embodiments, the invention uses electrical stimulation and/or chemical stimulation (e.g., one or more pharmaceuticals) to treat the neurological condition. In addition to electrical and/or chemical stimulation, magnetic stimulation and/or thermal as well as sound stimulation can also be used. Magnetic stimulation can be provided by internally implanted probes or by externally applied directed magnetic fields. Thermal stimulation can be provided by using implanted probes that are regulated to produce or emit heat and/or cold temperatures.

In certain embodiments, the present invention comprises a therapeutic stimulation system for treating neurological conditions or disorders having a surgically implanted device in communication with a predetermined site, which can be either a central neuronal or peripheral neuronal tissue site. The device can include an electrode, for example an electrode assembly or electrical stimulation lead. The electrode is coupled to a signal source (e.g., an electrical signal source), which, in turn, is operated to stimulate the predetermined site.

In certain embodiments, it is envisioned that the present invention comprises a method of treating a neurological disorder comprising the step of providing an electrical burst stimulus to a predetermined neuronal tissue site whereby the stimulus alters neuronal activity thereby treating the disorder.

The burst stimulus comprises a frequency in the range of about 1 Hz to about 300 Hz, more particular, in the range of about 1 Hz to about 18 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 2 to about 100 spikes, more particularly, about 2 to about 10 spikes. Each spike can comprise a frequency in the range of about 50 to 1000 Hz, more preferably in a range of 200 to 500 Hz. The interval between spikes (e.g., inter-spike interval) can be about 0.5 milliseconds to about 100 milliseconds. Preferably, the maximum inter-spike interval is 5 milliseconds. The frequency of the spikes within the burst does not need to be constant or regular, in fact, typically, the frequency of the spikes is random or variable.

In further embodiments, the burst stimulus is followed by an inter-burst interval or inter-group interval. The inter-burst interval has duration in the range of about 5 milliseconds to about 5 seconds, more preferably, about 10 milliseconds to about 300 milliseconds. Preferably, the minimum inter-group interval is 20 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In certain embodiments, the neuromodulation method can be used to treat neurological disorders or diseases that result from incorrect central nervous system control in which the disorder comprises a regular bursting rhythm. Such disorders having a regular bursting rhythm include, but are not limited to movement disorders such as Parkinson's Disease, epilepsy, tinnitus, central pain including phantom pain or other forms of deafferentation or central pain.

Still further, the neuromodulation method of the present invention can be used to treat neurological disorders or diseases that result from incorrect central nervous system control in which the disorder comprises an irregular bursting rhythm. Such disorders can include, but are not limited to dystonia or chorea. Still further, the neuromodulation method of the present invention can be used to treat neurological disorders or diseases that result from incorrect central nervous system control, and in which the methods corrects neuronal inbalances (inhibitory vs excitatory, high frequency vs low frequency (e.g., thalamocortical dysrhythmia), sympathetic vs parasympathetic).

The neuromodulation method of the present invention can also be used to alter a physiological and/or pathological signaling pattern. Those of skill in the art are aware that a physiological and/or pathological signaling pattern can be either regular or irregular. Thus, it is envisioned that the stimulation method as used herein can alter such patterns to alleviate the neurological condition or disease.

The neuromodulation method of the present invention can be used to modulate neuronal activity of any neuronal tissue within a patient. In certain embodiments, a device is surgically implanted in the patient such that the device is in communication with a predetermined neuronal tissue site, and the device is operated to stimulate the predetermined site. The device can include a probe, for example, electrode assembly (e.g., electrical stimulation lead). The proximal end of the probe is coupled to an electrical signal source, which, in turn, is operated to stimulate the predetermined treatment site.

Neuronal tissue includes any tissue associated with the peripheral nervous system or the central nervous system. Peripheral neuronal tissue can include a nerve root, root ganglion or other nerves, for example the median nerve, sympathetic nerve or vagal nerve, etc. Central neuronal tissue includes brain tissue, spinal tissue or brainstem tissue. Brain tissue can include thalamus/sub-thalamus, basal ganglia, hippocampus, amygdala, hypothalamus, mammilary bodies, substantia nigra or cortex or white matter tracts afferent to or efferent from the abovementioned brain tissue, inclusive of the corpus callosum. Spinal tissue can include the ascending and descending tracts of the spinal cord, more specifically, the ascending tracts of the spinal cord that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 3A illustrates an example of regular neuronal firing. FIG. 3B illustrates an example of a neuronal burst firing.

FIG. 4A illustrate an example of an regular burst firing pattern. FIG. 4B illustrate an example of a irregular burst firing pattern.

DETAILED DESCRIPTION OF THE INVENTION

I. Definitions

Figure 1A:
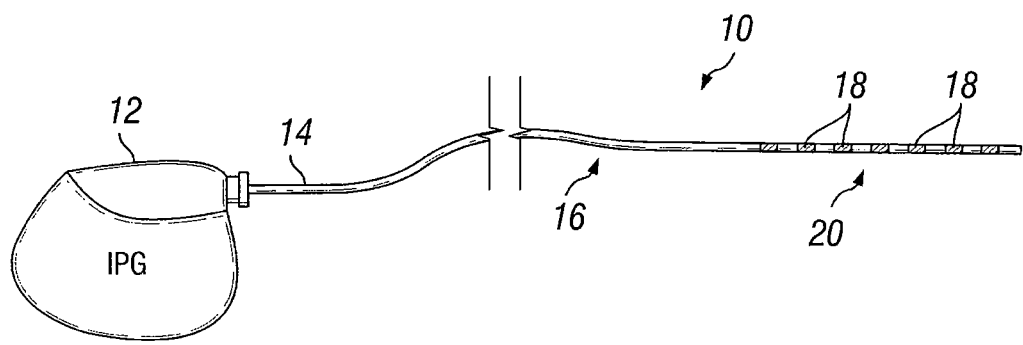
FIGS. 1A-1B illustrate example stimulation systems for electrically stimulating neuronal tissue.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having", "including", "containing" and "comprising" are interchangeable and one of skill in the art is cognizant that these terms are open ended terms.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. The predetermined site may be selected from the group consisting of the peripheral neuronal tissue or central neuronal tissue. Central neuronal tissue includes, but is not limited to brain tissue, brainstem, spinal tissue. Spinal tissue includes, the spinal cord, or the dorsal column of the spinal cord which may include the spinal cord area corresponding to cervical vertebral segments C1 to C8, thoracic vertebral segments T1 to T12, lumbar vertebral segments L1 and L2. One of ordinary skill in the art will understand that the spinal cord normally terminates at the second lumbar vertebrae L2. However, in certain subjects the spinal cord may terminate before or after the L2 vertebrae segment and that the present invention is intended for use along the entire length of the spinal cord.

As used herein, the use of the term "dorsal column" refers to conducting pathways in the spinal cord that are located in the dorsal portion of the spinal cord between the posterior horns, and which comprises afferent somatosensory neurons. The dorsal column is also known as the posterior funiculus.

As used herein, the use of the words "epidural space" or "spinal epidural space" is known to one with skill in the art, and refers to an area in the interval between the dural sheath and the wall of the spinal canal.

As used herein the term "modulate" refers to the ability to regulate positively or negatively neuronal activity. Thus, the term modulate can be used to refer to an increase, decrease, masking, altering, overriding or restoring of neuronal activity.

As used herein, the term "burst firing" or "burst mode" refers to an action potential that is a burst of high frequency spikes (300-1000 Hz) (Beurrier et al., 1999). Burst firing acts in a non-linear fashion with a summation effect of each spike. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that, possibly, occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

As used herein, the term "spike" refers to an action potential. Yet further, a "burst spike" refers to a spike that is preceded or followed by another spike within a short time interval (Matveev, 2000), in other words, there is an inter-spike interval, in which this interval is generally about 100 ms but can be shorter or longer, for example 0.5 milliseconds.

As used herein, the term "neuronal" refers to a cell which is a morphologic and functional unit of the brain, brainstem, spinal cord, and peripheral nerves.

As used herein, the term "peripheral neuronal tissue" refers to any neuronal tissue associated with a nerve root, root ganglion, or peripheral nerve that is outside the brain and the spinal cord. It includes the autonomic nervous system, inclusive of (ortho-)sympathetic and parasympathetic system.

As used herein, the term "central neuronal tissue" refers to neuronal tissue associated with the brain, spinal cord or brainstem.

As used herein, the term "neurology" or "neurological" refers to conditions, disorders, and/or diseases that are associated with the nervous system. The nervous system comprises two components, the central nervous system, which is composed of the brain and the spinal cord, and the peripheral nervous system, which is composed of ganglia and the peripheral nerves that lie outside the brain and the spinal cord. One of skill in the art realizes that the nervous system may be linguistically separated and categorized, but functionally the system is interconnected and interactive. Yet further, the peripheral nervous system is divided into the autonomic system (parasympathetic and sympathetic), the somatic system and the enteric system. Thus, any condition, disorder and/or disease that effect any component or aspect of the nervous system (either central or peripheral) are referred to as a neurological condition, disorder and/or disease. As used herein, the term "neurological" or "neurology" encompasses the terms "neuropsychiatric" or "neuropsychiatry" and "neuropsychological" or "neuropsychology". Thus, a neurological disease, condition, or disorder includes, but is not limited to tinnitus, epilepsy, depression, anxiety, Parkinson's Disease, autonomic dysfunctions, etc.

As used herein, the term "neuropsychiatry" or "neuropsychiatric" refers to conditions, disorders and/or diseases that relate to both organic and psychic disorders of the nervous system.

As used herein, the term "neuropsychological" or "neuropsychologic" or neuropsychology refers to conditions, disorders and/or disease that relate to the functioning of the brain and the cognitive processors or behavior.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the term "stimulate" or "stimulation" refers to electrical, chemical, magnetic, thermal and/or other such stimulation that modulates the predetermined neuronal sites.

As used herein, the term "treating" and "treatment" refers to modulating predetermined neuronal sites (central neuronal tissue and/or peripheral neuronal tissue) so that the subject has an improvement in the disease or condition, for example, beneficial or desired clinical results. For purposes of this invention, beneficial or desired clinical results include, but are not limited to, alleviation of symptoms, diminishment of extent of disease, stabilized (e.g., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Nervous System

The nervous system comprises two general components, the central nervous system, which is composed of the brain and the spinal cord, and the peripheral nervous system, which is composed of ganglia or dorsal root ganglia and the peripheral nerves that lie outside the brain and the spinal cord. One of skill in the art realizes that the nervous system may be linguistically separated and categorized, but functionally they are interconnected and interactive.

The central nervous system comprises the brain and spinal cord, which together function as the principal integrator of sensory input and motor output. In general terms, the brain consists of the cerebrum (cerebral hemispheres and the diencephalons), the brainstem (midbrain, pons, and medulla); and the cerebellum. It is well known that the cerebrum represents the highest center for sensory and motor and emotional and cognitive processing. In general, the frontal lobe processes motor, visual, speech, and personality modalities; the parietal lobe processes sensory information; the temporal lobe, auditory and memory modalities; and the occipital lobe vision. The cerebellum, in general, coordinates smooth motor activities and processes muscle position, while the brainstem conveys motor and sensory information and mediates important autonomic functions. These structures are of course integrated with the spinal cord which receives sensory input from the body and conveys somatic and autonomic motor information to peripheral targets. Thus, one of skill in the art realizes that the central nervous system is capable of evaluating incoming information and formulating response to changes that threaten the homeostasis of the individual.

The peripheral nervous system is divided into the autonomic system (parasympathetic and sympathetic), the somatic system and the enteric system. The term peripheral nerve is intended to include both motor and sensory neurons and neuronal bundles of the autonomic system, the somatic system, and the enteric system that reside outside of the spinal cord and the brain. Peripheral nerve ganglia and nerves located outside of the brain and spinal cord are also described by the term peripheral nerve.

A. Action Potentials and their Propagation

Information is conveyed through the nervous system via neuronal cells along their membranes and across synaptic junctions. Thus, the neuronal cells process information by both passive processes (e.g., electrical properties of the membrane which enable spatial and temporal summation) and active processes (e.g., propagation of the action potential, signal amplification or attenuation, and synaptic transmission). Generation of an action potential at the axon initial segment requires passive summation of multiple inputs, as well as signal amplification before membrane depolarization reaches threshold, thus the passive and active processes are interdependent.

The generation of the action potential initially depends upon the electrical properties of the cell. It is known that cells have an electrical voltage difference across their membranes, the membrane potential. Several types of protein pores or ion channels are responsible for maintaining and altering the membrane potential of the cell. Voltage-gated sodium channels, which have a low threshold, are responsible for the explosive depolarization of the membrane potential that forms the action potential or spike, whereas, the voltage-gated potassium channels are responsible for the repolarization of the membrane potential. For excitation, stimulatory input results in a net increase in the inward flow of sodium ions compared to an outward flow of potassium ions results in a depolarizing cell membrane potential change. For inhibitory inputs, potassium and chloride ion channels are opened which drives the membrane potential away from threshold (hyperpolarization). As one of skill in the art realizes neurons receive multiple excitatory and inhibitory inputs, thus summation of these inputs occurs, for example temporal and spatial summation. Temporal summation occurs when a series of subthreshold impulses in one excitatory fiber produces an action potential in postsynaptic cell. Spatial summation occurs when subthreshold impulses from two or more different fibers trigger an action potential.

Once the initial action potential is generated, the information is conveyed via axonal conduction or synaptic transmission (e.g., chemical or electrical). Electrical synapses are found not only in the brain, but in heart and smooth muscle and epithelial liver cells. However, in the brain, electrical synapses (also known as gap junctions) are less common than chemical synapses, and are characterized by rapid speed of transmission and do not readily allow inhibitory actions or long-lasting changes in effectiveness. Gap junctions allow the passage of not only ions, but other small molecules. In humans, astrocytes contain gap junctions to mediate potassium buffering, and they are also present in the retina, inferior olive, vestibular nuclei, nucleus of the trigeminal nerve, and the reticular nucleus of the thalamus.

Chemical synapses, on the contrary, do mediate either excitatory or inhibitory actions, and are generally considered more flexible. Another difference between chemical and electrical transmission is that electrical can be bidirectional since the ion channels connect the cytoplasm of the pre and postsynaptic cells, whereas chemical transmission is typically unidirectional since there is no continuity between the cells. Chemical synapses comprise a presynaptic element that contain vesicles comprising neurotransmitters and a postsynaptic element which contains receptors for the neurotransmitters. Transmitter release is initiated when the nerve terminal is depolarized by an action potential resulting in a rapid influx of calcium ions into the nerve terminal. This rapid influx of calcium ions cause fusion of the vesicles to the presynaptic membrane and ultimately release of the neurotransmitters which then bind to their receptor located on the postsynaptic membrane.

The ability of the neuronal cell to fire or produce action potentials may vary depending upon its biophysical properties (e.g., types of ionic channels, etc.) and/or its position in the circuit or nervous system. Thus, cells can respond to an input (stimulatory or inhibitory) with a decelerating train of action potentials, an accelerating train of action potentials or a constant firing frequency. For example, an increase in firing of a neuronal cell may be a result from increased amounts of calcium ions or a function of residual increase in calcium ions left over from the first stimulation (also known as facilitation) in the presynaptic element which results in increase release of neurotransmitter. Thus, a second stimulation can occur within milliseconds of the first. Conversely, a second stimulation may result in inhibition and not facilitation of the response if an inhibitory interneuron is activated which feedback to the first neuronal cell to inhibit firing.

B. Firing Modes

Figure 3A:
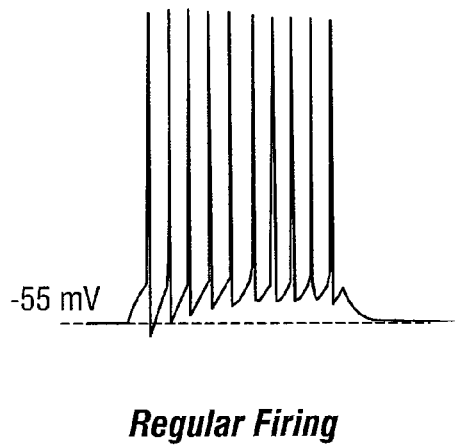
FIGS. 3A-3B illustrate example neuronal firings.

Different firing modes or frequencies occur in the brain and/or other neuronal tissue, for example tonic firing and burst firing (irregular or regular burst firing), as shown in FIGS. 3 and 4. The thalamus utilizes both types of firing modes. The two thalami (bilateral paired structures) are the gateways to the cerebral cortex and, thus, to consciousness. The thalamic nuclei specialize in several different signaling functions: transmitting signals from sensory input to the cortex; transmitting signals from cortical motor centers to effectors; transmitting control signals that select which input and output will be permitted to pass to and from the cortex and how the signals will be sequenced (thalamic reticular nuclei (TRN)); and modulating (controlling intensity) and synchronizing (grouping) the signals (Intralaminar Nuclei (ILN)).

All thalamic relay neurons pass through the TRN, which opens and closes their "gates" going to the cortex, (McAlonan and Brown, 2002). One mode that TRN neurons use to transmit these relays is burst firing mode. This mode is useful for activating a small population of neurons in the cortex for a short period. In contrast, the continuous (tonic) firing mode permits a thalamic neuron to transmit a steady stream of signals to the cortex. The tonic firing pattern triggers looping activation in the cortical circuits that receive the signals. Evoking looping, or "recurrent" activation in the cortex requires a steady neural input.

The ILN are a tiny cluster of cells in the central body of the thalamus, hidden inside of the "laminae," the white layers that separate the bigger nuclei of the thalamus. In contrast to the bigger relay nuclei, most of the ILN send signals that change the activity of the cortical receiving area (Sherman and Guillery, 2002). For example, an ILN might receive signals from one cortical area and send them on to several other cortical areas to increase excitation in the receiving areas (a cortico-thalamo-cortical pattern, C-T-C).

Tonic or burst firing mode may be related to the molecules which are associated with the neurons. Such molecules include either parvalbumin (an egg-derived protein also a calcium-binding protein) or calbindin (a calcium-binding protein). Tonic firing is found especially in cells that contain parvalbumin. It behaves in a linear fashion, for example, the auditory thalamus (MGBV) fires at a specific frequency and the auditory cortex will follow at the same pace with a minor phase difference (Miller et al., 2001) of 2 ms. Tonic firing, however, can be overruled by burst firing (Lisman 1997; Sherman 2001; Swadlow and Gusev 2001).

Burst firing is typically found in calbindin positive cells (Kawaguchi and Kubota 1993; Hu et al., 1994; Hu 1995; He and Hu 2002). Thus, burst mode firing may utilize a calbindin system to generate the burst. Generally, burst firing is accomplished through the activation of either a subthreshold membrane conductance that initiates action potentials or a suprathreshold membrane conductance that once activated evokes two or more action potentials. Sodium ($Na^+$) and calcium ($Ca^{2+}$) activated conductances have all been implicated in burst generation. Hippocampal (Wong and Stewart, 1992; Traub et al., 1994) and layer V neocortical (Schwindt and Crill, 1999) pyramidal cells may initiate somatic $Na^+$ action potentials from a slow $Ca^{2+}$ potential generated within the dendrites. Alternatively, bursts in subicular (Mattia et al., 1997) and sensorimotor cortical neurons (Franceschetti et al., 1995; Guatteo et al., 1996) may be generated through a voltage-dependent $Na^+$ conductance, independent of $Ca^{2+}$ (Brumberg, 2000).

Burst firing acts in a non-linear fashion (Lisman 1997; Sherman 2001; Swadlow and Gusev 2001) with a summation effect of each spike, thus more readily activating a target cell (Lisman 1997) than tonic firing. Burst firing has been described in drowsiness, slow wave sleep, and anesthesia (Steriade et al., 1989; McCormick and Feeser 1990), as well as epilepsy (Futatsugi and Riviello 1998; Huguenard 1999) in the thalamus, and it functionally shuts off external auditory sensory stimuli to gain access to the cortex (Edeline et al., 2000; Massaux and Edeline 2003; Massaux et al., 2004), though not completely (Edeline et al., 2000). Neural network modeling has further demonstrated that bursts are generated by positive feedback through excitatory connections (Tabak and Latham 2003). In networks of two populations, one excitatory and one inhibitory, decreasing the inhibitory feedback can cause the network to switch from a tonically active, asynchronous state to the synchronized bursting state (van Vreeswijk and Hansel 2001).

The generation of repetitive burst discharges in neurons is correlated with the generation of gamma frequency (30-70 Hz) oscillations in the local field potential (Gray and Singer, 1989). It is believed that conscious perception depends on gamma band frequency activity (Gray and Singer, 1989; Joliot, 1994; Steriade, 2000).

Increasing depolarization to hyperpolarization induces a prolonged refractory period of tonic firing resulting in single spike bursts (Ramcharan, Cox et al., 2000) (in the visual system), further depolarization results in progressively more spikes per burst (Ramcharan, Cox et al., 2000). Further depolarization will silence the cell (Beurrier, Congar et al., 1999).

The transient membrane hyperpolarization leads to activation of voltage dependent T type calcium channels generating low threshold calcium spikes. Riding on top of the low thresholds calcium spikes are bursts of sodium spikes mediated by fast voltage-gated sodium channels (Steriade and Llinas 1988). Calcium entry during the burst leads to calcium activated potassium channels then in combination with voltage gated potassium channels the membrane is repolarized (McCormick and Feeser 1990). The low threshold calcium spikes act as a pacemaker (Perez-Reyes 2003).

It is hypothesized according to the present invention that burst stimulation may be used by neuronal tissue to process information in a manner that is similar to amplitude modulation. Specifically, the spacing between individual bursts in a burst stimulus may be used to signal information to various regions in the brain. That is, the spacing between the bursts can vary (hence are "amplitude modulated") to convey information. The signaled information can be related to relevance information. The signaled information could also be related to signaling the beginning and ending of certain packets of information. By providing electrical burst stimulation from an implantable pulse generator, it is possible that the stimulated brain tissue will change its processing of other stimulus information. For example, by appropriately selecting an interburst interval, auditory information that would otherwise be problematic to a patient could become ignored by a respective segment of the brain due to a lack of "relevance" and/or a lack of synchronization with the arrival of the burst stimulus.

III. Electrical Stimulation Devices

Figure 1B:
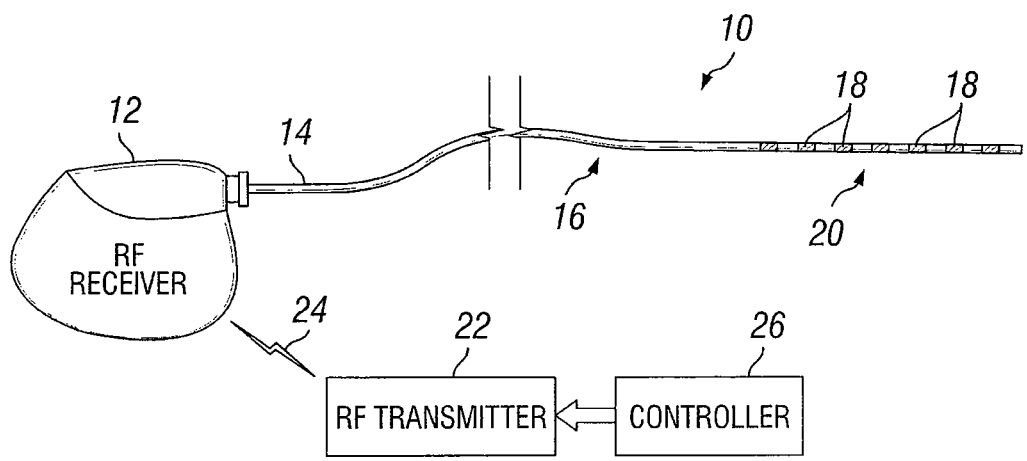
Figure 2A:
FIGS. 2A-2I illustrate example electrical stimulation leads that may be used to electrically stimulate neuronal tissue.
Figure 2B:
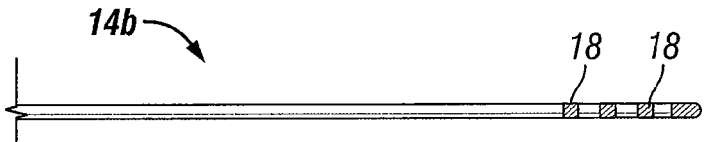
Figure 2C:
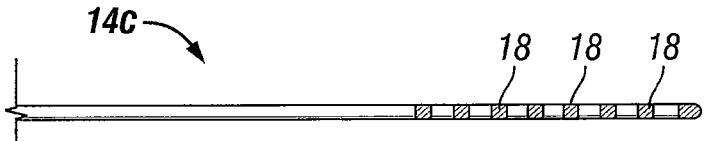
Figure 2D:
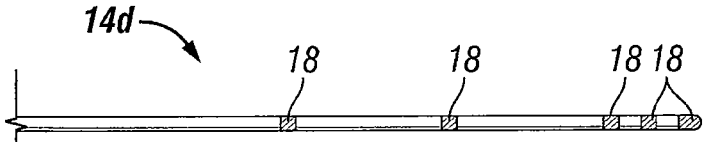
Figure 2E:
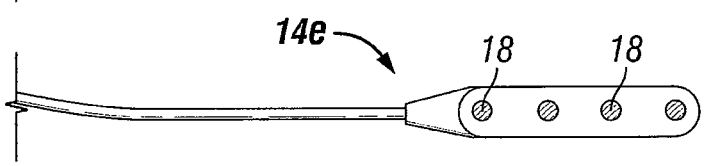
Figure 2F:
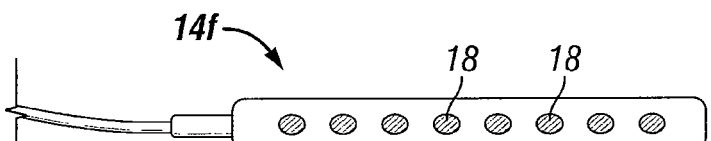
Figure 2G:
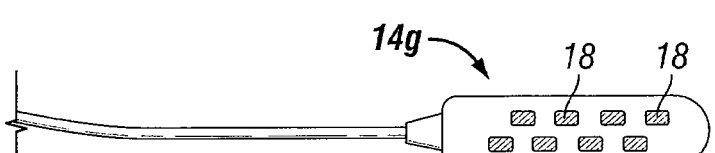
Figure 2H:
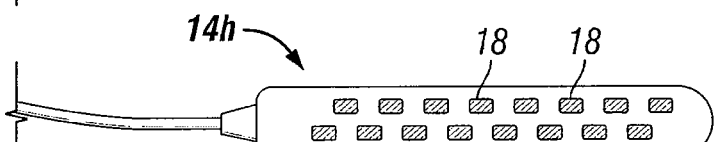
Figure 2I:
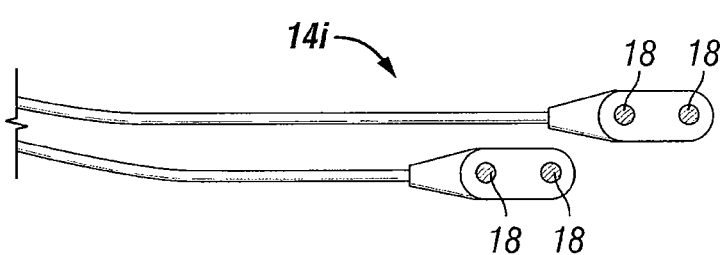

FIGS. 1A-1B illustrate example neurological stimulation systems 10 for electrically stimulating a predetermined site area to treat one or more neurological disorders or conditions. In general terms, stimulation system 10 includes an implantable pulse generating source or electrical stimulation source 12 and one or more implantable electrodes or electrical stimulation leads 14 for applying electrical stimulation pulses to the a predetermined site. In operation, both of these primary components are implanted in the person's body, as discussed below. In certain embodiments, stimulation source 12 is coupled directly to a connecting portion 16 of stimulation lead 14. In certain other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.).

As contemplated in the present invention, a predetermined site can include either peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves.

Central neuronal tissue includes brain tissue, spinal tissue or brainstem tissue. Brain tissue can include thalamus/subthalamus, basal ganglia, hippocampus, amygdala, hypothalamus, mammilary bodies, substantia nigra or cortex or white matter tracts afferent to or efferent from the abovementioned brain tissue, inclusive of the corpus callosum. Spinal tissue can include the ascending and descending tracts of the spinal cord, more specifically, the ascending tracts of that comprise intralaminar neurons or the dorsal column. The brainstem tissue can include the medulla oblongata, pons or mesencephalon, more particular the posterior pons or posterior mesencephalon, Lushka's foramen, and ventrolateral part of the medulla oblongata.

A doctor, the patient, or another user of stimulation source 12 may directly or indirectly input stimulation parameters to specify or modify the nature of the stimulation provided.

In one embodiment, as shown in FIG. 1A, stimulation source 12 includes an implantable pulse generator (IPG). One of skill in the art is aware that any commercially available implantable pulse generator can be used in the present invention, as well as a modified version of any commercially available pulse generator. Thus, one of skill in the art would be able to modify an IPG to achieve the desired results. An exemplary IPG is one that is manufactured by Advanced Neuromodulation Systems, Inc., such as the Genesis® System, part numbers 3604, 3608, 3609, and 3644. Another example of an IPG is shown in FIG. 1B, which shows stimulation source 12 including an implantable wireless receiver. An example of a wireless receiver may be one manufactured by Advanced Neuromodulation Systems, Inc., such as the Renew® System, part numbers 3408 and 3416. In another embodiment, the IPG can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. The wireless signals are represented in FIG. 1B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the signal parameters of electrical signals transmitted through electrical stimulation lead 14 to the stimulation site. Thus, the external controller 26 can be for example, a handheld programmer, to provide a means for programming the IPG. An example wireless transmitter 122 may be one manufactured by Advanced Neuromodulation Systems, Inc., such as the Renew® System, part numbers 3508 and 3516.

Conventional neuromodulation devices can be modified to apply burst stimulation to nerve tissue of a patient by modifying the software instructions stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

These conventional neuromodulation devices can be adapted by programming the microprocessor to deliver a number of spikes (relatively short pulse width pulses) that are separated by an appropriate interspike interval. Thereafter, the programming of the microprocessor causes the pulse generation module to cease pulse generation operations for an interburst interval. The programming of the microprocessor also causes a repetition of the spike generation and cessation of operations for a predetermined number of times. After the predetermined number of repetitions have been completed, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the interspike interval, the interburst interval, the number of bursts to be repeated in succession, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, a neuromodulation device can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

FIGS. 2A-2I illustrate example stimulation leads 14 that may be used for electrically stimulating the predetermined site to treat one or more neurological disorders or conditions. As described above, each of the one or more stimulation leads 14 incorporated in stimulation system 10 includes one or more stimulation electrodes 18 adapted to be positioned in communication with the predetermined site and used to deliver to the stimulation pulses received from stimulation source 12. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (e.g., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site in one side of the head, while bilateral electrical stimulation of the predetermined site may be accomplished using two stimulation leads 14 implanted in communication with the predetermined site in opposite sides of the head.

In one embodiment, the stimulation source is transcutaneously in communication with the electrical stimulation lead. In "transcutaneous" electrical nerve stimulation (TENS), the stimulation source is external to the patient's body, and may be worn in an appropriate fanny pack or belt, and the electrical stimulation lead is in communication with the stimulation source, either remotely or directly. In another embodiment, the stimulation is percutaneous. In "percutaneous" electrical nerve stimulation (PENS), needles are inserted to an appropriate depth around or immediately adjacent to a predetermined stimulation site, and then stimulated.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc.

The preferred neurostimulation devices should allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

Figure 3B:
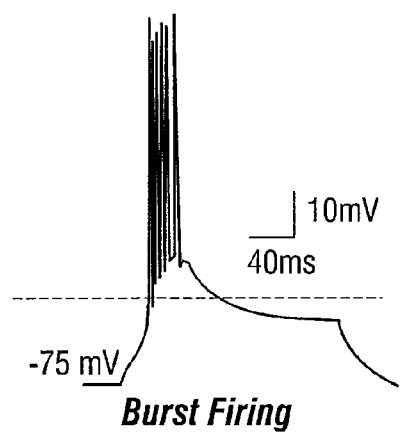

In the present invention, the stimulation parameter of signal frequencies are varied to achieve a burst type rhythm, or burst mode stimulation, as shown in FIG. 3B. Generally, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. One skilled in the art will further realize that each burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. One of skill in the art is aware that the frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween.

Figure 4A:
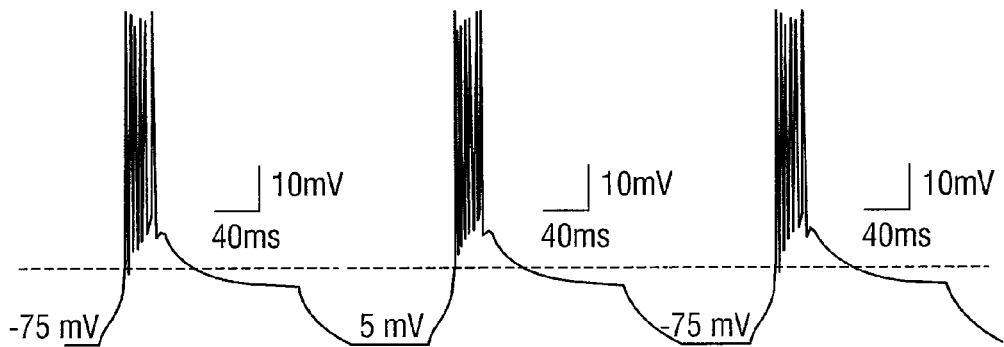
FIG. 4A-4B illustrate examples of burst firing.
Figure 4B:
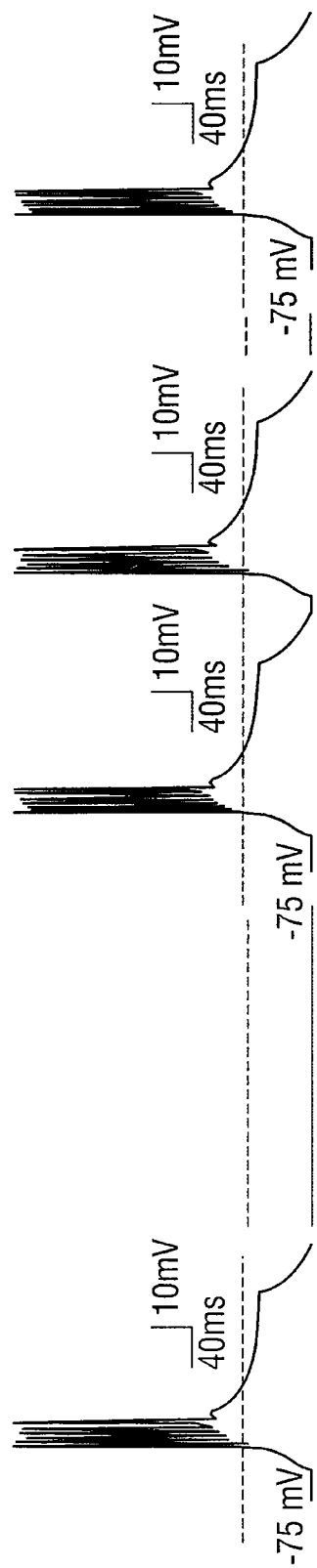

The burst stimulus can be followed by an inter-burst interval, as shown in FIGS. 4A-4B. The inter-burst interval has duration in the range of about 5 milliseconds to about 5 seconds, more preferably, 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics), as shown in FIGS. 4A-4B. More specifically, the burst stimulus can have a physiological pattern or a pathological pattern.

It is envisaged that the patient will require intermittent assessment with regard to patterns of stimulation. Different electrodes on the lead can be selected by suitable computer programming, such as that described in U.S. Pat. No. 5,938, 690, which is incorporated by reference here in full. Utilizing such a program allows an optimal stimulation pattern to be obtained at minimal voltages. This ensures a longer battery life for the implanted systems.

IV. Implantation of Electrical Devices

The stimulation system 10, described above, can be implanted into a person's body with stimulation lead 14 located in communication with a predetermined site. It is envisioned that the predetermined site can be a central or peripheral neuronal tissue.

A. Deep Brain Stimulation

In certain embodiments, for example, patients who are to have an electrical stimulation lead or electrode implanted into the brain, generally, first have a stereotactic head frame, such as the Leksell, CRW, or Compass, mounted to the patient's skull by fixed screws. However, frameless techniques may also be used. Subsequent to the mounting of the frame, the patient typically undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The current way to do this is to rigidly mount the head frame to the surgical table. Subsequently, a series of reference points are established to relative aspects of the frame and patient's skull, so that either a person or a computer software system can adjust and calculate the correlation between the real world of the patient's head and the virtual space model of the patient MRI scans. The surgeon is able to target any region within the stereotactic space of the brain with precision (e.g., within 1 mm). Initial anatomical target localization is achieved either directly using the MRI images or functional imaging (PET or SPECTscan, fMRI, MSI), or indirectly using interactive anatomical atlas programs that map the atlas image onto the stereotactic image of the brain. As is described in greater detail elsewhere in this application, the anatomical targets or predetermined site may be stimulated directly or affected through stimulation in another region of the brain.

In preferred embodiments, the predetermined site or implant sites include, but are not limited to thalamus/subthalamus, basal ganglia, hippocampus, amygdala, hypothalamus, mammilary bodies, substantia nigra or cortex or white matter tracts afferent to or efferent from the abovementioned brain tissue, inclusive of the corpus callosum. Still further, the predetermined site may comprise the auditory cortex and/or somatosensory cortex in which the stimulation devices is implanted cortically.

Based upon the coordinates, the electrical stimulation lead 14 can be positioned in the brain. Typically, an insertion cannula for electrical stimulation lead 14 is inserted through the burr hole into the brain, but a cannula is not required. For example, a hollow needle may provide the cannula. The cannula and electrical stimulation lead 14 may be inserted together or lead 14 may be inserted through the cannula after the cannula has been inserted.

Once electrical stimulation lead 14 has been positioned in the brain, lead 14 is uncoupled from any stereotactic equipment present, and the cannula and stereotactic equipment are removed. Where stereotactic equipment is used, the cannula may be removed before, during, or after removal of the stereotactic equipment. Connecting portion 16 of electrical stimulation lead 14 is laid substantially flat along the skull. Where appropriate, any burr hole cover seated in the burr hole may be used to secure electrical stimulation lead 14 in position and possibly to help prevent leakage from the burr hole and entry of contaminants into the burr hole. Example burr hole covers that may be appropriate in certain embodiments are illustrated and described in co-pending U.S. application Ser. Nos. 11/010,108 and 11/010,136, both filed Dec. 10, 2004 and entitled "Electrical Stimulation System and Associated Apparatus for Securing an Electrical Stimulation Lead in Position in a Person's Brain", both of which are incorporated herein in their entirety.

Once electrical stimulation lead 14 has been inserted and secured, connecting portion 16 of lead 14 extends from the lead insertion site to the implant site at which stimulation source 12 is implanted. The implant site is typically a subcutaneous pocket formed to receive and house stimulation source 12. The implant site is usually positioned a distance away from the insertion site, such as near the chest, below the clavicle or alternatively near the buttocks or another place in the torso area. Once all appropriate components of stimulation system 10 are implanted, these components may be subject to mechanical forces and movement in response to movement of the person's body. A doctor, the patient, or another user of stimulation source 12 may directly or indirectly input signal parameters for controlling the nature of the electrical stimulation provided.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting an example stimulation system 10 into a person for electrical stimulation of the person's brain.

B. Spinal and Peripheral Neuronal Tissue

Electrical energy can be delivered through electrodes positioned external to the dura layer surrounding the spinal cord. Stimulation on the surface of the cord (subdurally) is also contemplated, for example, stimulation may be applied to the dorsal columns as well as to the dorsal root entry zone or the dorsal root ganglia and/or nerve root. Any area of the spinal cord may be stimulated in the present invention for example the any neuronal tissue associated with any of the cervical vertebral segments (C1, C2, C3, C4, C5, C6, C7 and C8) and/or any tissue associated with any of the thoracic vertebral segments (T1, T2, T3, T4, T5, T6, T7, T8, T9, T10, T11, 12) and/or any tissue associated with any of the lumbar vertebral segments (L1, L2, L3, L4. L5, L6) and/or any tissue associated with the sacral vertebral segments (S1, S2, S3, S4, S5). Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves. In addition peripheral nerves also includes the nerves of the autonomic nervous system, including both sympathetic and parasympathetic system Stimulation electrodes 18 may be positioned in various body tissues and in contact with various tissue layers; for example, subdural, subarachnoid, epidural, cutaneous, transcutaneous and subcutaneous implantation is employed in some embodiments. The electrodes are carried by two primary vehicles: a percutaneous leads and a laminotomy lead.

In certain embodiments, one or more stimulation electrodes 18 are positioned in communication with a peripheral nerve. Stimulation electrodes 18 are commonly positioned in communication with the peripheral nerve by electrodes applied cutaneously to the dermatome area of a peripheral nerve. Stimulation electrodes 18 can be positioned subcutaneously in communication with the peripheral nerve or on the nerve root ganglion.

For spinal cord stimulation, percutaneous leads commonly have two or more, equally-spaced electrodes, which are placed above the dura layer through the use of a Touhy-like needle. For insertion, the Touhy-like needle is passed through the skin, between desired vertebrae, to open above the dura layer. For unilateral stimulation, percutaneous leads are positioned on a side of a spinal column corresponding to the "afflicted" side of the body, as discussed above, and for bilateral stimulation, a single percutaneous lead is positioned along the patient midline (or two or more leads are positioned on each side of the midline).

An example of an eight-electrode percutaneous lead is an OCTRODE® lead manufactured by Advanced Neuromodulation Systems, Inc. A stimulation system such as is described in U.S. Pat. No. 6,748,276 is also contemplated.

Laminotomy leads have a paddle configuration and typically possess a plurality of electrodes (for example, two, four, eight, or sixteen) arranged in one or more columns. An example of a sixteen-electrode laminotomy lead is shown in FIG. 2.

Implanted laminotomy leads are commonly transversely centered over the physiological midline of a patient. In such position, multiple columns of electrodes are well suited to address both unilateral and bilateral stimulation requirements, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body. Unlike the needle-delivered percutaneous leads, laminotomy leads have a paddle configuration. The paddle typically possess a plurality of electrodes (for example, two, four, eight, or sixteen) arranged in some pattern, for example, columns. An example of an eight-electrode, two column laminotomy lead is a LAMITRODE® 44 lead manufactured by Advanced Neuromodulation Systems, Inc.

In the context of conventional spinal cord stimulation, the surgical procedure, or partial laminectomy, requires the resection and removal of certain vertebral tissue to allow both access to the dura and proper positioning of a laminotomy lead. Depending on the position of insertion, however, access to the dura may only require a partial removal of the ligamentum flavum at the insertion site.

If necessary, stimulation source 12 may be coupled directly to connecting portion 16 of stimulation lead 14. Alternatively, as described above and if necessary, stimulation source 12 may not be coupled directly to stimulation lead 14 and may instead be coupled to stimulation lead 14 via an appropriate wireless link. Of course, as those skilled in the art know, an embedded stimulation system will not need to be so coupled.

C. Brainstem Stimulation

The stimulation system 10, described above, can be implanted into a person's body with stimulation lead 14 located in communication with a predetermined brainstem tissue and/or area. Such systems that can be used are described in WO2004062470, which is incorporated herein by reference in its entirety.

The predetermined brainstem tissue can be selected from medulla oblongata, pons or mesencephalon, more particular the posterior pons or posterior mesencephalon, Lushka's foramen, and ventrolateral part of the medulla oblongata.

Implantation of a stimulation lead 14 in communication with the predetermined brainstem area can be accomplished via a variety of surgical techniques that are well known to those of skill in the art. For example, an electrical stimulation lead can be implanted on, in, or near the brainstem by accessing the brain tissue through a percutaneous route, an open craniotomy, or a burr hole. Where a burr hole is the means of accessing the brainstem, for example, stereotactic equipment suitable to aid in placement of an electrical stimulation lead 14 on, in, or near the brainstem may be positioned around the head. Another alternative technique can include, a modified midline or retrosigmoid posterior fossa technique.

In certain embodiments, electrical stimulation lead 14 is located at least partially within or below the aura mater adjacent the brainstem. Alternatively, a stimulation lead 14 can be placed in communication with the predetermined brainstem area by threading the stimulation lead up the spinal cord column, as described above, which is incorporated herein.

As described above, each of the one or more leads 14 incorporated in stimulation system 10 includes one or more electrodes 18 adapted to be positioned near the target brain tissue and used to deliver electrical stimulation energy to the target brain tissue in response to electrical signals received from stimulation source 12. A percutaneous lead 14 may include one or more circumferential electrodes 18 spaced apart from one another along the length of lead 14. Circumferential electrodes 18 emit electrical stimulation energy generally radially in all directions and may be inserted percutaneously or through a needle. The electrodes 18 of a percutaneous lead 14 may be arranged in configurations other than circumferentially, for example as in a "coated" lead 14. A laminotomy or paddle style lead 14, such as example leads 14e-i, includes one or more directional electrodes 18 spaced apart from one another along one surface of lead 14. Directional electrodes 18 emit electrical stimulation energy in a direction generally perpendicular to the surface of lead 14 on which they are located. Although various types of leads 14 are shown as examples, the present invention contemplates stimulation system 10 including any suitable type of lead 14 in any suitable number, including three-dimensional leads and matrix leads as described below. In addition, the leads may be used alone or in combination.

Yet further, a stimulation lead 14 can be implanted in communication with the predetermined brainstem area by a using stereotactic procedures similar to those described above, which are incorporated herein, for implantation via the cerebrum.

Still further, a predetermined brainstem area can be indirectly stimulated by implanting a stimulation lead 14 in communication with a cranial nerve (e.g., olfactory nerve, optic, nerve, oculomotor nerve, trochlear nerve, trigeminal nerve, abducent nerve, facial nerve, vestibulocochlear nerve, glossopharyngeal nerve, vagal nerve, accessory nerve, and the hypoglossal nerve) as well as high cervical nerves (cervical nerves have anastomoses with lower cranial nerves) such that stimulation of a cranial nerve indirectly stimulates the predetermined brainstem tissue. Such techniques are further described in U.S. Pat. Nos. 6,721,603; 6,622,047; and 5,335,657, and U.S. Provisional Application 60/591,195 entitled "Stimulation System and Method for Treating a Neurological Disorder" each of which are incorporated herein by reference.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting stimulation system 10 into a person for electrical stimulation of the predetermined site.

V. Infusion Pumps

In further embodiments, it may be desirable to use a drug delivery system independently or in combination with electrical stimulation to result in the stimulation parameters of the present invention. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 all of which are incorporated by reference in their entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877, which are incorporated herein by reference in their entirety.

Still further, the present invention can comprise a chemical stimulation system that comprises a system to control release of neurotransmitters (e.g., glutamate, acetylcholine, norepinephrine, epinephrine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined rate and amount in order to control the system parameter.

Sensor may comprise a sensor, sensor electrical components for providing power to the sensor and generating the sensor signal, a sensor communication system for carrying the sensor signal to controller, and a sensor housing for enclosing the electrical components and the communication system. Controller may include one or more programmable processors, logic circuits, or other hardware, firmware or software components configured for implementing the control functions described herein, a controller communication system for receiving the sensor signal from the sensor, and a controller housing for enclosing the controller communication system and the one or more programmable processors, logic circuits, or other hardware, firmware or software components. The infusion formulation delivery device may include a suitable infusion pump, infusion pump electrical components for powering and activating the infusion pump, an infusion pump communication system for receiving commands from the controller, and an infusion pump housing for enclosing the infusion pump, infusion pump electrical components, and infusion pump communication system. Such systems are described in U.S. Pat. No. 6,740,072, which is incorporated herein by reference in its entirety.

In certain embodiments, the sensor can be an electrode that senses a hyperactive burst pattern of activity or tonic firing, which in turns stimulates the infusion pump to release a chemical or stimulating drug or agent to modify the neuronal activity. The chemical or stimulating agent can be either an inhibiting agent or stimulating agent Herein, stimulating drugs comprise medications, anesthetic agents, synthetic or natural peptides or hormones, neurotransmitters, cytokines and other intracellular and intercellular chemical signals and messengers, other agents such as zinc and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., flouxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts, anesthetics (e.g., lidocane), and magnesium may also be used in combination with electrical stimulation.

VI. Treating Neurological Conditions

The present stimulation system and/or method acts to stimulate neuronal tissue which in turn stimulate the brain and cause/allow the brain to act in the best interest of the host through use of the brain's natural mechanisms. The prior art fails to recognize that stimulation of at least one the predetermined areas using the stimulation parameters of the present invention can provide the therapeutic treatments according to the instant invention.

Accordingly, the present invention relates to modulation of neuronal activity to affect neurological, neuropsychological or neuropsychiatric activity. The present invention finds particular application in the modulation of neuronal function or processing to affect a functional outcome. The modulation of neuronal function is particularly useful with regard to the prevention, treatment, or amelioration of neurological, psychiatric, psychological, conscious state, behavioral, mood, and thought activity (unless otherwise indicated these will be collectively referred to herein as "neurological activity" which includes "psychological activity" or "psychiatric activity"). When referring to a pathological or undesirable condition associated with the activity, reference may be made to a neurological disorder which includes "psychiatric disorder" or "psychological disorder" instead of neurological activity or psychiatric or psychological activity. Although the activity to be modulated usually manifests itself in the form of a disorder such as a attention or cognitive disorders (e.g., Autistic Spectrum Disorders); mood disorder (e.g., major depressive disorder, bipolar disorder, and dysthymic disorder) or an anxiety disorder (e.g., panic disorder, posttraumatic stress disorder, obsessive-compulsive disorder and phobic disorder); neurodegenerative diseases (e.g., multiple sclerosis, Alzheimer's disease, amyotrophic lateral sclerosis (ALS), Parkinson's disease, Huntington's Disease, Guillain-Barre syndrome, myasthenia gravis, and chronic idiopathic demyelinating disease (CID)), movement disorders (e.g., dyskinesia, tremor, dystonia, chorea and ballism, tic syndromes, Tourette's Syndrome, myoclonus, drug-induced movement disorders, Wilson's Disease, Paroxysmal Dyskinesias, Stiff Man Syndrome and Akinetic-Ridgid Syndromes and Parkinsonism), epilepsy, tinnitus, pain, phantom pain, diabetes neuropathy, one skilled in the art appreciates that the invention may also find application in conjunction with enhancing or diminishing any neurological or psychiatric function, not just an abnormality or disorder. Neurological activity that may be modulated can include, but not be limited to, normal functions such as alertness, conscious state, drive, fear, anger, anxiety, repetitive behavior, impulses, urges, obsessions, euphoria, sadness, and the fight or flight response, as well as instability, vertigo, dizziness, fatigue, photofobia, concentration dysfunction, memory disorders, headache, dizziness, irritability, fatigue, visual disturbances, sensitivity to noise (misophonia, hyperacusis, phonofobia), judgment problems, depression, symptoms of traumatic brain injury (whether physical, emotional, social or chemical), autonomic functions, which includes sympathetic and/or parasympathetic functions (e.g., control of heart rate), somatic functions, and/or enteric functions. Thus, the present invention encompasses modulation of central and/or peripheral nervous systems.

Other neurological disorders can include, but are not limited to headaches, for example, migraine, trigeminal autonomic cephalgia (cluster headache (episodic and chronic)), paroxysmal hemicrania (epidsodic and chronic), hemicrania continua, SUNCT (shortlasting unilateral neuralgiform headache with conjunctival injection and tearing), cluster tic syndrome, trigeminal neuroalgia, tension type headache, idiopathic stabbing headache, etc. The neurostimulation device can be implanted intracranially or peripherally, for example, but not limited to implanting a neurostimulation device occipitally for the treatment of headaches.

Autonomic and/or enteric nervous system disorders that can be treated using the stimulation system and/or method of the present invention include, but are not limited to hypertension, neurosis cordis or heart rhythm disorders, obesity, gastrointestinal motion disorders, respiratory disorders, diabetes, sleep disorders, snoring, incontinence both urologic and gastrointestinal, sexual dysfunction, chronic fatigue syndrome, fibromyalgia, whiplash associated symptoms, post-concussion syndrome, posttraumatic stress disorder etc.

Yet further immunological disorders may also be treated using the stimulation system and/or method of the present invention. This is based on the fact that the immune system senses antigens coordinates metabolic, endocrine and behavioral changes that support the immune system and modulates the immune system via neuroendocrine regulation and direct immune cell regulation. Such immunological disorders include, such as allergy, rhinitis, asthma, rheumatoid arthritis, psoriasis arthritis, lupus erythematosus disseminatus, multiple sclerosis and other demyelinating disorders, autoimmune thyroiditis, Crohn's disease, diabetis melitus etc.

Yet further tumoral disorders, both malignant and benign may also be treated using the stimulation system and/or method of the present invention. This is based on the fact that tumoral behavior is linked to immunological function. This is seen in immunodeficiency syndromes such as AIDS and hematological disorders, where multiple and different tumors develop. In this setting neuromodulation could indirectly influence tumoral behavior.

Yet further neuroendocrine disorders may also be treated using the stimulation system and/or method of the present invention. Such disorders are stress reactions, hypothalamic-pituitary axis dysfunction, etc Yet further functional disorders may also be treated using the stimulation system and/or method of the present invention. Such disorders can be anorexia, boulemia, phobias, addictions, paraphilia, psychosis, depression, bipolar disorder, kleptomania, aggression, or antisocial sexual behavior. One skilled in the art appreciates that the invention may also find application in conjunction with enhancing or diminishing any neurological or psychiatric function, not just an abnormality or disorder.

The present invention finds particular utility in its application to human neurological disorders, for example psychological or psychiatric activity/disorder and/or physiological disorders. One skilled in the art appreciates that the present invention is applicable to other animals which exhibit behavior that is modulated by the neuronal tissue. This may include, for example, primates, canines, felines, horses, elephants, dolphins, etc. Utilizing the various embodiments of the present invention, one skilled in the art may be able to modulate neuronal functional outcome to achieve a desirable result.

One technique that offers the ability to affect neuronal function is the delivery of electrical and/or chemical and/or magnetic stimulation for neuromodulation directly to target tissues or predetermined neuronal sites via an implanted device having a probe. The probe can be stimulation lead or electrode assembly. The electrode assembly may be one electrode, multiple electrodes, or an array of electrodes in or around the target area. The proximal end of the probe is coupled to a system to operate the device to stimulate the target site. Thus, the probe is coupled to an electrical signal source, which, in turn, is operated to stimulate the target tissue or predetermined site.

A predetermined site is a neuronal tissue, which can include either peripheral neuronal tissue and/or central neuronal tissue. Neuronal tissue includes any tissue associated with the peripheral nervous system or the central nervous system. Peripheral neuronal tissue can include a nerve root or root ganglion or any neuronal tissue that lies outside the brain, brainstem or spinal cord. Central neuronal tissue includes brain tissue, spinal tissue or brainstem tissue.

Peripheral nerves can include, but are not limited to olfactory nerve, optic, nerve, oculomotor nerve, trochlear nerve, trigeminal nerve, abducens nerve, facial nerve, vestibulocochlear (auditory) nerve, glossopharyngeal nerve, vagal nerve, accessory nerve, hypoglossal nerve, suboccipital nerve, the greater occipital nerve, the lesser occipital nerve, the greater auricular nerve, the lesser auricular nerve, the phrenic nerve, brachial plexus, radial axillary nerves, musculocutaneous nerves, radial nerves, ulnar nerves, median nerves, intercostal nerves, lumbosacral plexus, sciatic nerves, common peroneal nerve, tibial nerves, sural nerves, femoral nerves, gluteal nerves, thoracic spinal nerves, obturator nerves, digital nerves, pudendal nerves, plantar nerves, saphenous nerves, ilioinguinal nerves, gentofemoral nerves, and iliohypogastric nerves. Also all sympathetic and parasympathetic nerves and all sympathetic and parasympathetic parts of peripheral nerves.

Brain tissue can include thalamus/sub-thalamus (all thalamic nuclei, inclusive of medial and lateral geniculate body, intralaminar nuclei, nucleus reticularis, pulvinar, etc) basal ganglia (inclusive of putamen, caudate nucleus, globus pallidus), hippocampus, amygdala, hypothalamus, epithalamus, mammilary bodies, substantia nigra or cortex or white matter tracts afferent to or efferent from the abovementioned brain tissue, inclusive of the corpus callosum, formix, internal capsula, anterior and posterior commissural, cerebral peduncles etc. Brain tissue also includes cerebellum, inclusive of cerebellar peduncles, and cerebeller nuclei such as fastigial nucleus, globose nucleus, dentate nucleus, emboliform nucleus. Brain tissue also includes auditory cortex and the somatosensory cortex.

Spinal tissue can include the ascending and descending tracts of the spinal cord, more specifically, the ascending tracts of that comprise intralaminar neurons or the dorsal column, fsciculus gracilis and cuneatus, dorsolateral fasciculus of Lissauer, spinocerebellar and cerebellospinal tracti, spinothalamic, spinoolivary, spinotectal and spinoreticular tracti. Also inclusive are the rubrospinal, reticulospinal, vestibulospinal, tectospinal and corticospinal tracti and the medial longitudinal fasciculus etc. Any area of the spinal cord may be stimulated in the present invention for example the any neuronal tissue associated with any of the cervical vertebral segments (C1, C2, C3, C4, C5, C6, C7) and/or any tissue associated with any of the thoracic vertebral segments (T1, T2, T3, T4, T5, T6, T7, T8, T9, T10, T11, 12) and/or any tissue associated with any of the lumbar vertebral segments (L1, L2, L3, L4. L5, L6) and/or any tissue associated with the sacral vertebral segments (S1, S2, S3, S4, S5).

The brainstem tissue can include the medulla oblongata, pons or mesencephalon, more particular the posterior pons or posterior mesencephalon, Lushka's foramen, and ventrolateral part of the medulla oblongata inclusive of the cranial nerve nuclei, the reticular formatio, substantia nigra, red nucleus, the periaquaductal grey. This is also inclusive of white matter tracts such as the medial longitudinal fasciculus, lemniscus medialis, trigeminalis, spinalis and lateralis and sinothalamic, spinocerebellar, corticospinal and corticonuclear tracti, etc.

Using the stimulation system of the present invention, the predetermined site or target area is stimulated in an effective amount or effective treatment regimen to decrease, reduce, modulate or abrogate the neurological disorder. Thus, a subject is administered a therapeutically effective stimulation so that the subject has an improvement in the parameters relating to the neurological disorder or condition including subjective measures such as, for example, neurological examinations and neuropsychological tests (e.g., Minnesota Multiphasic Personality Inventory, Beck Depression Inventory, Mini-Mental Status Examination (MMSE), Hamilton Rating Scale for Depression, Wisconsin Card Sorting Test (WCST), Tower of London, Stroop task, MADRAS, CGI, N-BAC, or Yale-Brown Obsessive Compulsive score (Y-BOCS)), motor examination, and cranial nerve examination, and objective measures including use of additional psychiatric medications, such as anti-depressants, or other alterations in cerebral blood flow or metabolism and/or neurochemistry.

Patient outcomes may also be tested by health-related quality of life (HRQL) measures: Patient outcome measures that extend beyond traditional measures of mortality and morbidity, to include such dimensions as physiology, function, social activity, cognition, emotion, sleep and rest, energy and vitality, health perception, and general life satisfaction. (Some of these are also known as health status, functional status, or quality of life measures.)

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

In certain embodiments, in connection with improvement in one or more of the above or other neurological disorders, the electrical stimulation may have a "brightening" effect on the person such that the person looks better, feels better, moves better, thinks better, and otherwise experiences an overall improvement in quality of life.

In certain embodiments, it is envisioned that the present invention provides at least one burst stimulus (e.g., electrical, chemical, magnetic and/or thermal) to a predetermined neuronal tissue site whereby the stimulus alters neuronal activity thereby treating the disorder or condition. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 2 to about 100 spikes, more particularly, about 2 to about 10 spikes. Each spike can comprise a frequency in the range of about 1 Hz to about 1000 Hz, more particularly, in the range of about 50 to about 200 Hz or in the range of about 200 Hz to about 500 Hz. Those of skill in the art understand that the frequency for each spike within a burst can vary. Yet further, the spike interval can also vary from about 0.5 milliseconds to about 100 milliseconds.

In further embodiments, the burst stimulus is followed by an inter-burst interval. The inter-burst interval has duration in the range of about 5 milliseconds to about 5 seconds, more preferably, about 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In further embodiments, the stimulation system of the present invention can incorporate an infusion or drug delivery device. The device can contain a sensor, for example an electrode, that senses a hyperactive burst pattern of activity, which in turns stimulates the infusion pump to release a chemical or stimulating drug or agent to modify the neuronal activity. The chemical or stimulating agent can be either an inhibiting agent or stimulating agent, as described above.

In addition to electrical stimulation and/or chemical stimulation, other forms of stimulation can be used, for example magnetic, or thermal or combinations thereof. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Thermal stimulation can be provided by using implanted probes that are regulated for heat and/or cold temperatures which can stimulate or inhibit neuronal activity, for example, U.S. Pat. No. 6,567,696, which is incorporated herein by reference in its entirety.

The neuromodulation method of the present invention can be used to alter a physiological and/or pathological signaling pattern. Thus, it is envisioned that the stimulation method as used herein can alter such patterns to alleviate the neurological condition or disease, or to improve or enhance a desired physiological function (e.g., self confidence, alleviating shyness, distrust etc).

In certain embodiments, the neuromodulation method can be used to treat neurological disorders or diseases that result from incorrect central nervous system control in which the disorder comprises a regular bursting rhythm. Such disorders having a regular bursting rhythm include, but are not limited to Parkinson's, epilepsy, tinnitus and phantom pain or other forms of deafferentation or central pain. Thus, it is envisioned that the neuromodulation of the present invention will alter or disrupt the regular bursting rhythm associated with the disorder.

In further embodiments, it is envisioned that other central neuronal tissue may be stimulated, for example, tissue associated with the spinal cord, more specially the dorsal horn or column to treat any neurological condition or disorder associated with innervations from such, for example, pain. It is known that deafferented dorsal horn cells fire in a burst mode firing (Guenot 2003), which namely adding a valence to the high frequency tonic information (Jeanmonod 1989; Swadlow 2001, Sherman 2001). Thus, the present invention can modulate or disrupt the burst mode firing of the dorsal horn in such conditions thereby treating the condition.

Still further, it is contemplated that the neuromodulation system of the present invention can be used to alter the firing mode for predetermined peripheral neuronal tissue. For example, it is known that brief bursts that come from the periphery can more reliably transmit neural information between primary afferent fibers and spinal dorsal horn neurons (Wan 2004). One of the reasons might be that in contrast to tonic firing (both low frequency—1 Hz—or high frequency—100 Hz), burst firing releases BDNF (brain derived neurotrophic factor) from dorsal horn cells (Lever 2001), which is known to be part of a general mechanism for activity-dependent modification of synapses in the developing and adult nervous system. Thus, diseases of abnormal trophic support (such as neurodegenerative diseases) and diseases of abnormal excitability (such as epilepsy and central pain sensitization) can be related in some cases to abnormal BDNF signaling (Binder 2004). As such, it is envisioned that stimulation of peripheral neuronal tissue using the stimulation parameters or neuromodulation system of the present invention will alter, override, or disrupt the burst firing, thus altering release of BDNF, thereby treating the neurological condition or disorder.

Still further, it is known that the sympathetic system fires in bursts, and the parasympathetic system as well. Any neurological or non-neurological disorder associated with a hypoactive, hyperactive or maladaptive sympathetic or parasympathetic firing can be modified using this method.

Still further, the neuromodulation method of the present invention can be used to treat neurological disorders or diseases that result from incorrect central nervous system control in which the disorder comprises an irregular bursting rhythm. Such disorders can include, but are not limited to dystonia or chorea or hallucinations. Thus, it is envisioned that such conditions are caused or linked to arrhythmic burst firing or desynchronized tonic firing can be treated utilizing the neuromodulation system or stimulation parameters of the present invention.

In different motor, sensory and autonomic neurological disorders two mechanisms might be involved: the firing rate is altered in tonic and burst firing cells and the amount of burst firing is increased. A second mechanism involved is an alteration in the synchrony of neuronal firing, which is often increased.

Thus, burst firing neuromodulation is indicated for modifying both physiological or abnormal tonic and burst firing in the brain, brainstem, spinal cord and peripheral nervous system, inclusive of the autonomic system. This type of neuromodulation can be modify burst firing patterns, but also for tonic firing patterns A. Sensory Disorders 1. Tinnitus In the auditory system, tonic firing transmits the contents of auditory information, while burst firing transmit the valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Tinnitus is a noise in the ears, often described as ringing, buzzing, roaring, or clicking. Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise.

Tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002; Zacharek et al., 2002; Kaltenbach et al., 2004), inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also the burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that the present invention can be used to modify burst firing, thus modifying tonic gamma activity.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in the present invention, it is envisioned that the neuromodulation system can attack either of these two pathways: slowing down tonic firing in the lemniscal system (below 40 Hz) or removing the valence attached to it by the extralemniscal system by suppressing the regular bursting rhythm, thereby treating tinnitus. Yet further, the neuromodulation system of the present invention can also make the tinnitus disappear via auditory habituation. Suppressing the rhythmic burst firing in the frontal cortex may alter the emotional affect given to the tinnitus, with the tinnitus persisting, a situation known by many people perceiving tinnitus, but without much influence on their daily life. Such methods of treating tinnitus are further described in U.S. Provisional applications entitled "Deep Brain Stimulation to Treat Tinnitus" filed Oct. 21, 2004; "Peripheral Nerve Stimulation to Treat Tinnitus" filed Oct. 21, 2004; and "Dorsal Column Stimulation to Treat Tinnitus" filed Oct. 21, 2004, each of which is incorporated by reference in its entirety.

2. Phantom Pain

In phantom pain the same is noted as in Parkinson's Disease (PD) and tinnitus. In humans, the tonic firing rate increases (Yamashiro et al., 2003), as well as the amount of burst firing in the deafferented receptive fields (Rinaldi et al., 1991; Jeanmonod et al., 1996; Radhakrishnan et al., 1999) in the somatosensory thalamic nuclei (Rinaldi et al., 1991; Lenz et al., 1998), as well as activity in the in the intralaminar nuclei (Weigel and Krauss 2004). Synchrony in firing is also increased. This is similar to what is seen in animal neuropathic pain models (Lombard and Besson 1989; Nakamura and Atsuta 2004) (Yamashiro et al., 1991). These results suggest that in pain decreased spike frequency adaptation and increased excitability develops after injury to sensory neurons. Through decreased $Ca^{2+}$ influx, the cell becomes less stable and more likely to initiate or transmit bursts of action potentials (McCallum et al., 2003).

Thus, it is envisioned that that the neuromodulation system or method of the present invention will alter or disrupt the regular bursting rhythm associated with the phantom pain.

3. Motor Disorders

In Parkinson's disease (PD), the striatum is viewed as the principal input structure of the basal ganglia, while the internal pallidal segment (GPi) and the substantia nigra pars reticulata (SNr) are output structures. Input and output structures are linked via a monosynaptic "direct" pathway and a polysynaptic "indirect" pathway involving the external pallidal segment (GPe) and the subthalamic nucleus (STN). According to current schemes, striatal dopamine (DA) enhances transmission along the direct pathway (via D1 receptors), and reduces transmission over the indirect pathway (via D2 receptors) (Wichmann and DeLong 2003).

Increased firing rates are noted in PD, both in the globus pallidus (Magnin et al., 2000) and the subthalamic nucleus (Levy et al., 2002) and is reversed in successful STN stimulation in PD (Welter et al., 2004; Boraud et al., 1996). Synchronization between firing rates is important: lower frequency oscillations facilitate slow idling rhythms in the motor areas of the cortex, whereas synchronization at high frequency restores dynamic task-related cortical ensemble activity in the gamma band (Brown 2003). In PD, a (hyper) synchronization is related to tremor (Levy et al., 2002), similarly to what is seen in the animal Parkinson model (Raz et al., 2000; Nini et al., 1995).

Two or more firing modes exist in the subthalamic nucleus: tonic firing (68%), phasic or burst firing (25%) and phasic-tonic (7%) (Magarinos-Ascone et al., 2002).

In the monkey MPTP Parkinson model, burst firing, which occurs at 4 to 8 Hz, increases in the STN and Gpi in comparison to normal firing (from 69% and 78% in STN and GPi to 79% and 89%, respectively) (Bergman et al., 1994), as well as burst duration, without increase in the amount of spikes per burst (Bergman et al., 1994). Abnormally increased tonic and phasic activity in STN leads to abnormal GPi activity and is a major factor in the development of parkinsonian motor signs (Wichmann et al., 1994). The percentage of cells with 4- to 8-Hz periodic activity correlates with tremor and is significantly increased from 2% to 16% in STN and from 0.6% to 25% in GPi with the MPTP treatment (Bergman et al., 1994). These cells are also recorded in humans with PD (Hutchison et al., 1997). Furthermore, synchronization increases, e.g., a decrease in independent activity (Raz et al., 2000; Nini et al., 1995), both in tonically firing cells (Raz et al., 2001) and burst firing cells. Thus, it is envisioned that that the neuromodulation or stimulation system or method of the present invention will alter or disrupt or override the regular bursting rhythm associated with PD.

Other movement disorders, for example, chorea, Huntington's chorea, hemiballism and parkinsonian tremor all differ in the amount of regularity in their muscle contractions. (Hashimoto and Yanagisawa 1994). The regularities of interval, amplitude, rise time, and EMG activity differs within order of regularity, such PD, vascular chorea, Huntington chorea and hemiballism being least regular (Hashimoto and Yanagisawa 1994). However, in chorea (Hashimoto et al., 2001), hemiballism (Postuma and Lang 2003) and Huntington's disease (Cubo et al., 2000), the firing rate might be decreased in contrast to PD. Burst discharges are, however, correlated to the choreatic movements (Kanazawa et al., 1990), similarly to what is noted in PD (Bergman, Wichmann et al., 1994). Thus, the neuromodulation system and/or method of the present invention is used to alter or disrupt the dysfunctional firing rate of the disease or condition.

B. Autonomic Disorders

The autonomic nervous system (ANS) is predominantly an efferent system transmitting impulses from the central nervous system (CNS) to peripheral organ systems. Its effects include control of heart rate and force of contraction, constriction and dilatation of blood vessels, contraction and relaxation of smooth muscle in various organs, visual accommodation, pupillary size and secretions from exocrine and endocrine glands. In addition to it being predominantly an efferent system, there are some afferent autonomic fibers (e.g., transmit information from the periphery to the CNS), which are concerned with the mediation of visceral sensation and the regulation of vasomotor and respiratory reflexes, for example the baroreceptors and chemoreceptors in the carotid sinus and aortic arch which are important in the control of heart rate, blood pressure and respiratory activity. These afferent fibers are usually carried to the CNS by major autonomic nerves such as the vagus, splanchnic or pelvic nerves, although afferent pain fibers from blood vessels may be carried by somatic nerves.

The ANS is divided into two separate divisions, the parasympathetic and sympathetic systems. This division is based on anatomical and functional differences. Both of these systems consist of myelinated preganglionic fibres that make synaptic connections with unmyelinated postganglionic fibres, and it is these which then innervate the effector organ. These synapses usually occur in clusters called ganglia. Most organs are innervated by fibers from both divisions of the ANS, and the influence is usually opposing (e.g., the vagus slows the heart, whilst the sympathetic nerves increase its rate and contractility), although it may be parallel (e.g., the salivary glands).

The activity recorded from mammalian sympathetic nerves comes in bursts, which result from large numbers of fibers firing synchronously. Human sympathetic nerve activity behaves similarly. Vasomotor, cardiac and sudomotor nerve fibers all fire in bursts. Bursts in post-ganglionic nerves are driven by synchronously firing preganglionic neurons. Burst amplitude, which reflects the number of fibers firing together, and burst probability are controlled independently (McAllen and Malpas 1997). The sympathetic nerve also fires in a 10 Hz tonic mode (Barman, Kitchens et al., 1997). This 10-Hz rhythm is also involved in cardiovascular regulation, as blood pressure falls significantly when the 10-Hz rhythm is eliminated. Cardiac-related burst activity and 10-Hz rhythms are generated by different pools of brainstem neurons (Barman, Kitchens et al., 1997).

When electrical stimulation is applied to the sympathetic nerve, burst stimulation is more powerful (vasoconstrictor) than tonic mode. The amount of spikes per burst also determines the efficacy of stimulation (Ando, Imaizumi et al., 1993). The same is seen with electrical stimulation of the cervical sympathetic nerve trunk delivered at 50 Hz in bursts of 1 s every 10 s. Burst stimulation evoked a more copious, uniform and reproducible flow of saliva than when delivered at 10 Hz continuously (Anderson, Garrett et al., 1988). Similar superior results with burst stimulation have been obtained studying nasal mucosa reactivity: both types of stimulation reduced nasal blood flow and volume, but the responses were significantly larger with burst stimulation at 0.59 Hz compared to tonic 0.59 Hz stimulation (Lacroix, Stjarne et al., 1988).

In the parasympathetic system, burst firing and tonic firing co-exist. For example, one population of neurons responds with a brief burst of action potentials at the onset of the depolarization, accommodating to the stimulus, and the other population responds with repetitive action potentials persisting throughout the duration of the stimulus, not accommodating to the stimulus (Myers 1998; Bertrand 2004).

Burst stimulation at 0.1 Hz with 20 Hz spiking of the parasympathetic nerve results in a 200-fold more powerful enzyme induction than 2 Hz tonic stimulation, when delivering the same amount of pulses (in the sublingual gland) (Nilsson, Rosengren et al., 1991).

1. Hypertension and Heart Rhythm Disorders

The nucleus of the solitary tract (NTS), a termination site for primary afferent fibers from baroreceptors and other peripheral cardiovascular receptors, and the paratrigeminal nucleus (Pa5) contain blood pressure-sensitive neurons, some of which have rhythmic activity locked to the cardiac cycle, making them key components of the central pathway for cardiovascular regulation. NTS and Pa5 baroreceptor-activated neurons possess phasic discharge patterns locked to the cardiac cycle (Junior, Caous et al., 2004). The human insular cortex is involved in cardiac regulation. The left insula is predominantly responsible for parasympathetic cardiovascular effects. On stimulation of the left insular cortex, parasympathetic tone increases resulting in bradycardia and depressor responses more frequently than tachycardia and pressor effects ($p<0.005$) (Oppenheimer, Gelb et al., 1992). The converse applies for the right insular cortex: stimulation of the human right insula increases sympathetic cardiovascular tone (Oppenheimer 1993). Acute left insular stroke increases basal cardiac sympathetic tone and is associated with a decrease in randomness of heart rate variability (Oppenheimer, Kedem et al., 1996). Increased sympathoadrenal tone, resulting from damage to cortical areas involved in cardiac and autonomic control can induce cardiac damage by nonischemic mechanisms (Oppenheimer and Hachinski 1992).

Brain noradrenaline (NA) neurons in the locus coeruleus (LC) and major parts of the SNS respond by burst activation in concert to stressful stimuli implying novelty or fear. (Svensson 1987). In hypertension, burst firing is increased (Schlaich, Lambert et al., 2004) (Esler, Rumantir et al., 2001).

The autonomic nervous system plays an important role in the genesis of various cardiac rhythm disorders. In patients with paroxysmal atrial fibrillation, it is important to distinguish vagally mediated from adrenergically mediated atrial fibrillation. The former is considered to represent a form of lone atrial fibrillation affecting particularly males aged 40 to 50 years. The arrhythmic episodes manifest themselves most often during the night lasting from minutes to hours, whereas in adrenergic mediated atrial fibrillation, atrial fibrillation is often provoked by emotional or physical stress. (Hohnloser, van de Loo et al., 1994)

Thus, hypertension (e.g., neurogenic hypertension) can be treated with burst stimulation of the left insula using the stimulation system of the present invention. In a similar fashion, bradycardia can be treated by burst stimulation of the right insula as subjects with bradycardia have significantly higher metabolic activity in the right (p<0.0001) and in the left temporal insula (p<0.015) than those with normal heart rates (Volkow, Wang et al., 2000). Lone atrial fibrillation can be treated by either by left or rightsided burst stimulation depending on whether it is vagally or adrenergicly induced.

2. Sleep Apnea

Activity in the sympathetic nervous system is enhanced not only in obstructive apnea, but also in central and mixed apnea (Shimizu, Takahashi et al., 1997). Burst rate during apnea is higher in central apneas than in obstructive apneas. Burst rate is the central component of mixed apnea and the obstructive component of mixed apneas (Shimizu, Takahashi et al., 1997).

This intense sympathoexcitation is due to chronic or intermittent hypoxia (Cutler, Swift et al., 2004; Cutler, Swift et al., 2004). Pathological sympathoexcitation appears to depend on both recruitment and increased burst firing frequency. In OSAS, also the amount of spikes per burst is increased, (Elam, McKenzie et al., 2002) and at night, arousal-induced reduction in sympathetic burst latency is noted (Xie, Skatrud et al., 1999).

Functional MRI or FMRI studies demonstrate reduced neural signals within the frontal cortex, anterior cingulate, cerebellar dentate nucleus, dorsal pons, anterior insula and lentiform nuclei. Signal increases in OSA over control subjects are seen in the dorsal midbrain, hippocampus, quadrangular cerebellar lobule, ventral midbrain and ventral pons (Macey, Macey et al., 2003). In the rat, the respiratory area in the anterior insular cortex consist of two distinct zones which overlap a region modulating the gastrointestinal activity (Aleksandrov, Aleksandrova et al., 2000). In the more rostral area, there is a decrease in respiratory airflow and tidal volume with no alteration of the respiratory rate (the inhibition response), and in the other there is an increase in respiratory rate and inspiratory airflow (the excitation response).

Thus, the present invention can be used to activate respiration during apneas by burst stimulation of the anterior insula.

C. Obesity

Food presentation in normal healthy, non-obese individuals significantly increases metabolism in the whole brain (24%, P<0.01), and these changes are largest in superior temporal, anterior insula, and orbitofrontal cortices (Wang, Volkow et al., 2004). Food-related visual stimuli elicit greater responses in the amygdala, parahippocampal gyms and anterior fusiform gyms when participants are in a hungry state relative to a satiated state (LaBar, Gitelman et al., 2001). Hunger is associated with significantly increased rCBF in the vicinity of the hypothalamus and insular cortex and in additional paralimbic and limbic areas (orbitofrontal cortex, anterior cingulate cortex, and parahippocampal and hippocampal formation), thalamus, caudate, precuneus, putamen, and cerebellum (Tataranni, Gautier et al., 1999). Satiation is associated with increased rCBF in the vicinity of the ventromedial prefrontal cortex, dorsolateral prefrontal cortex, and inferior parietal lobule (Tataranni, Gautier et al., 1999). High-calorie foods yield significant activation within the medial and dorsolateral prefrontal cortex, thalamus, hypothalamus, corpus callosum, and cerebellum. Low-calorie foods yield smaller regions of focal activation within medial orbitofrontal cortex, primary gustatory/somatosensory cortex, and superior, middle, and medial temporal regions (Killgore, Young et al., 2003). Activity within the temporo-insular cortex in normal appetitive function is associated with the desirability or valence of food stimuli, prior to ingestion (Gordon, Dougherty et al., 2000). When a food is eaten to satiety, its reward value decreases. Responses of gustatory neurons in the secondary taste area within the orbitofrontal cortex are modulated by hunger and satiety, in that they stop responding to the taste of a food on which an animal has been fed to behavioral satiation, yet may continue to respond to the taste of other foods (Critchley and Rolls 1996; O'Doherty, Rolls et al., 2000). In the OFC, the rCBF decreases in the medial OFC and increases in the lateral OFC as the reward value of food changes from pleasant to aversive for non-liquid (Small, Zatorre et al., 2001) and liquid foods (Kringelbach, O'Doherty et al., 2003). In the insular gustatory cortex, neuronal responses to gustatory stimuli are not influenced by the normal transition from hunger to satiety. This is in contrast to the responses of a population of neurons recorded in the hypothalamus, which only respond to the taste of food when the monkey is hungry (Yaxley, Rolls et al., 1988). Brain responses to hunger/satiation in the hypothalamus, limbic/paralimbic areas (commonly associated with the regulation of emotion), and prefrontal cortex (thought to be involved in the inhibition of inappropriate response tendencies) might be different in obese and lean individuals (Del Parigi, Gautier et al., 2002). Compared with lean women, obese women have significantly greater increases in rCBF in the ventral prefrontal cortex and have significantly greater decreases in the paralimbic areas and in areas of the frontal and temporal cortex (Gautier, Del Parigi et al., 2001). In obese women, the rCBF is higher in the right parietal and temporal cortices during the food exposure than in the control condition. In addition, in obese women the activation of the right parietal cortex is associated with an enhanced feeling of hunger when looking at food (Karhunen, Lappalainen et al., 1997). This significantly higher metabolic activity in the bilateral parietal somatosensory cortex is noted in the regions where sensation to the mouth, lips and tongue are located. The enhanced activity in somatosensory regions involved with sensory processing of food in the obese subjects can make them more sensitive to the rewarding properties of food related to palatability and can be one of the variables contributing to their excess food consumption (Wang, Volkow et al., 2002).

Based on the abovementioned model, the stimulation system and/or method of the present invention can be used to produce burst stimulation of the—orbitofrontal cortex or—insula to treat obesity especially in those people who are constant eaters rather than binge or high volume eaters. Other targets that can be stimulated are the dorsolateral prefrontal cortex, thalamus, hypothalamus, corpus callosum, and cerebellum, as well as the medial orbitofrontal cortex, primary gustatory/somatosensory cortex, and superior, middle, and medial temporal regions and the amygdalohippocampal area and anterior cingulated area.

D. Cognitive and Psychological Disorders

1. Depression

In patients suffering from a depression, a hypometabolism and hypoperfusion localized to the left middorsolateral frontal cortex (MDLFC) is noted (Baxter, Schwartz et al., 1989; Brody, Saxena et al., 2001). Furthermore decreased neural activity in the MDLFC, aka the dorsolateral prefrontal cortex, is correlated with severity of depression (Bench, Friston et al., 1992; Bench, Friston et al., 1993; Dolan, Bench et al., 1994) and is reversed upon recovery from depression (Bench, Frackowiak et al., 1995). Electroencephalography demonstrates increased alpha power. Alpha power is thought to be inversely related to neural activity in left frontal regions of the brains of depressed patients (Bruder, Fong et al., 1997).

Metabolic activity in the ventral perigenual ACC is increased in depressed patients relative to control subjects (Videbech, Ravnkilde et al., 2001) and is positively correlated with severity of depression (Drevets 1999). Furthermore, neural activity in this region decreases in response to antidepressant treatment (Brody, Saxena et al., 2001).

The MDLFC occupies the middle frontal and superior frontal gyri and comprises cytoarchitectonic areas 46 and 9/46 (middle frontal gyrus) and area 9 (superior frontal gyrus) (Paus and Barrett 2004). The MDLFC has connections with sensory areas processing visual (prestriate and inferior temporal cortices), auditory (superior temporal cortex) and somatosensory (parietal cortex) information (Petrides and Pandya 1999). The MDLFC also reciprocally connects with the anterior and, to a lesser extent, posterior cingulate cortices (Bates and Goldman-Rakic 1993).

Transcranial magnetic stimulation has been performed in the treatment of depression. The left MDLFC is the most common target for rTMS treatment of depression (Paus and Barrett 2004), and rTMS of the left MDLFC modulates the blood-flow response in the ACC (Barrett, Della-Maggiore et al., 2004; Paus and Barrett 2004). High-frequency (20 Hz) and low-frequency (1 Hz) stimulation seem to have an opposite effect. High-frequency stimulation (HFS) increases and low-frequency stimulation (LFS) decreases cerebral blood flow (CBF) and/or glucose metabolism in the frontal cortex and other linked brain regions (Speer, Kimbrell et al., 2000; Kimbrell, Little et al., 1999; and Post, Kimbrell et al., 1999).

Successful treatment of depression with TMS results in normalization of hypoperfusion (with HFS) and normalization hyperperfusion (with LFS) (Kimbrell, Little et al., 1999). Thus, TMS treatment for depression can be proposed using 20 Hz left frontal cortex (Kimbrell, Little et al., 1999; Paus and Barrett 2004) or 1 Hz right frontal cortex (Klein, Kreinin et al., 1999).

In the ACC of the rat, three kinds of burst firing is recorded. Rhythmic burst firing with inter-burst intervals of 80 and 200 ms and non rhythmic burst firing (Gemmell, Anderson et al., 2002). ACC stimulations evoke both tonic and burst reactions in the dorsolateral prefrontal cortex (Desiraju 1976). Similarly to other cortical areas, the dorsolateral prefrontal cortex has burst firing cells, tonic firing cells and mixed firing cells. Similarly to other areas, the burst firing notices new incoming sensory (auditory, visual) information, and tonic firing continues as long as the stimulus lasts (Ito 1982). TMS in burst mode is more powerful than TMS in tonic mode. For example, 20 seconds of 5 Hz burst firing with 3 pulses at 50 Hz per burst have the same effect as 10 minutes 1 Hz tonic TMS.

Thus, the present stimulation system and/or method can be used to treat depression. For example, a cortical electrode is implanted on the right MDLFC and a 5 Hz burst mode is used to treat recurring depressions that react to a test stimulation with TMS.

2. Obsessive Convulsive Disorder

Obsessive-compulsive disorder is a worldwide psychiatric disorder with a lifetime prevalence of 2% and mainly characterized by obsessional ideas and compulsive behaviors and rituals. Bilateral stimulation in the anterior limbs of the internal capsules (Nuttin, Cosyns et al., 1999; Nuttin, Gabriels et al., 2003) or nucleus accumbens stimulation (Sturm, Lenartz et al., 2003) can improve symptoms but at high frequency and high intensity stimulation. Thus, the present invention can be used to produce burst mode stimulation to treat an obsessive-compulsive disorder.

3. Tourette's Syndrome

Tourette syndrome (TS) is a neuropsychiatric disorder with onset in early childhood. It is characterized by tics and often accompanied by disturbances in behavior, such as obsessive-compulsive disorder (OCD). Bilateral thalamic stimulation, with promising results on tics and obsessive-compulsive symptoms has been performed as a treatment. (Visser-Vandewalle, Temel et al., 2003; Temel and Visser-Vandewalle 2004). Thus, it is envisioned that the stimulation system and/or method of the present invention can be used to treat TS.

VII. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example

Burst Mode Neuromodulation Using TMS

It has been demonstrated that white noise does not react to electrical stimulation of the auditory cortex (De Ridder, De Mulder et al. 2005). Transcranial magnetic stimulation (TMS) is capable of verifying tinnitus suppression in a non-invasive way (Plewnia, Bartels et al. 2003; De Ridder, Verstraeten et al. 2005). However, effects of tonic transcranial magnetic simulation on synaptic plasticity are often weak, highly variable between individuals, and rarely last longer than 30 min. Theta burst TMS on the other hand produces a controllable, consistent, long-lasting, and powerful effect on motor cortex physiology and behavior after an application period of only 20-190 s (Huang, Edwards et al. 2005). In other words it is a more powerful way of modifying brain functioning.

To demonstrate that the above, 22 patients with unilateral white noise or narrow band tinnitus were evaluated using both tonic and burst mode transcranial magnetic stimulation (TMS). Tinnitus attenuation was measured using a Visual Analog Scale, and the amount of tinnitus suppression was compared using both stimulation settings.

Three patients were excluded because of a placebo positive result, 10 patients did not demonstrate a tinnitus suppression, neither with tonic, nor with burst TMS, so 9 patients were finally included for comparison.

Average tinnitus suppression in these patients was 8.3% for tonic mode, and 54.5% for burst mode, a statistically significant difference (Wilcoxon matched pairs test, $Z=2.520504$, $p=0.012$ (0.011719)), demonstrating the clinical superiority of burst mode stimulation for treating tinnitus.

REFERENCES CITED

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Application No. 60/528,604
U.S. Application No. 60/528,689
U.S. Pat. No. 5,335,657
U.S. Pat. No. 5,938,690

U.S. Pat. No. 6,567,696
U.S. Pat. No. 6,622,047
U.S. Pat. No. 6,671,555
U.S. Pat. No. 6,690,974
U.S. Pat. No. 6,721,603
U.S. Pat. No. 6,740,072
U.S. Pat. No. 6,748,276
Alain, C., D. L. Woods, et al., (1998). Brain Res 812(1-2): 23-37.
Alho, K. (1995). Ear Hear 16(1): 38-51.
Bandrowski, A. E., S. L. Moore, et al., (2002). Synapse 44(3): 146-57.
Beurrier, C., P. Congar, et al., (1999). J Neurosci 19(2): 599-609.
Binder, Adv Exp Med Biol. 2004; 548:34-56.
Brozoski, T. J., C. A. Bauer, et al., (2002). J Neurosci 22(6): 2383-90.
Brumberg, The Journal of Neuroscience, 20 (13):4829-4843), 2000
Brumberg, The Journal of Neuroscience, Jul. 1, 2000, 20(13): 4829-4843.
Cazals, Y., K. C. Horner, et al., (1998). J Neurophysiol 80(4): 2113-20.
Chen, G. D. and P. J. Jastreboff (1995). Hear Res 82(2): 158-78.
Chernigovskii, V. N., S. S. Musyashchikova, et al., (1979). Biol Bull Acad Sci USSR 6(1): 1-7.
Condon, C. D. and N. M. Weinberger (1991). Behav Neurosci 105(3): 416-30.
Cooper, D. C. (2002). Neurochem Int 41(5): 333-40.
Coro, F., P. E. M, et al., (1998). J Exp Biol 201(Pt 20): 2879-2890.
Coutinho, V. and T. Knopfel (2002). Neuroscientist 8(6): 551-61.
De Ridder, D., G. De Mulder, et al. (2005). ORL in press.
De Ridder, D., E. Verstraeten, et al. (2005). Otol Neurotol 26(4): 616-619.
Huang, Y. Z., M. J. Edwards, et al. (2005). Neuron 45(2): 201-6.
Plewnia, C., M. Bartels, et al. (2003). Ann Neurol 53(2): 263-6.
Csepe, V., G. Karmos, et al., (1987). Electroencephalogr Clin Neurophysiol 66(6): 571-8.
Deouell, L. Y., S. Bentin, et al., (1998). Psychophysiology 35(4): 355-65.
Diamond, D. M. and N. M. Weinberger (1984). Behav Neurosci 98(2): 189-210.
Disney, A. and M. B. Calford (2001). J Neurophysiol 86(2): 1052-6.
Edeline, J. M., N. Neuenschwander-el Massioui, et al., (1990). Behav Brain Res 39(2): 145-55.
Edeline, J. M., Y. Manunta, et al., (2000). J Neurophysiol 84(2): 934-52.
Eggermont, J. J. (1990). Hear Res 48(1-2): 111-23.
Eggermont, J. J. (2003). Auris Nasus Larynx 30 Suppl: S7-12.
Eggermont, J. J. and M. Kenmochi (1998). Hear Res 117(1-2): 149-60.
Fairhall, A. L., G. D. Lewen, et al., (2001). Nature 412(6849): 787-92.
Feig, S. L. (2004). J Comp Neurol 468(1): 96-111.
Fischer, C., D. Morlet, et al., (2000). Audiol Neurootol 5(3-4): 192-7.
Franceschetti et al., Brain Res. 1995 Oct. 23; 696(1-2):127-39.
Futatsugi, Y. and J. J. Riviello, Jr. (1998). Brain Dev 20(2): 75-9.
Gerken, G. M. (1996). Hear Res 97(1-2): 75-83.
Givois, V. and G. S. Pollack (2000). J Exp Biol 203 Pt 17: 2529-37.
Gopal, K. V. and G. W. Gross (2004). Hear Res 192(1-2): 10-22.
Gray and Singer, Proc Natl Acad Sci USA. 1989 March; 86(5):1698-702.
Guatteo et al., Brain Res. 1996 Nov. 25; 741(1-2):1-12.
He, J. (1997). J Neurophysiol 77(2): 896-908.
He, J. (2003). Exp Brain Res 153(4): 579-90.
He, J. and B. Hu (2002). J Neurophysiol 88(4): 2152-6.
He, J., Y. Q. Yu, et al., (2002). J Neurophysiol 88(2): 1040-50.
Hsieh, C. Y., S. J. Cruikshank, et al., (2000). Brain Res 880 (1-2): 51-64.
Hu, B. (1995). J Physiol 483 (Pt 1): 167-82.
Hu, B., V. Senatorov, et al., (1994). J Physiol 479 (Pt 2): 217-31.
Huguenard, J. R. (1999). Adv Neurol 79: 991-9.
Jastreboff, P. J. (1990). Neurosci Res 8(4): 221-54.
Jastreboff, P. J. and C. T. Sasaki (1986). J Acoust Soc Am 80(5): 1384-91.
Jastreboff, P. J., J. F. Brennan, et al., (1988). Laryngoscope 98(3): 280-6.
Javitt, D. C., M. Steinschneider, et al., (1994). Brain Res 667(2): 192-200.
Javitt, D. C., M. Steinschneider, et al., (1996). Proc Natl Acad Sci USA 93(21): 11962-7.
Jeanmonod, D., M. Magnin, et al., (1996). Brain 119 (Pt 2): 363-75.
Joliot et al., Proc Natl Acad Sci USA. 1994 Nov. 22; 91(24): 11748-51.
Jongsma, M. L., C. M. Van Rijn, et al., (1998). Eur J Pharmacol 341(2-3): 153-60.
Kaltenbach, J. A. and C. E. Afman (2000). Hear Res 140(1-2): 165-72.
Kaltenbach, J. A., D. A. Godfrey, et al., (1998). Hear Res 124(1-2): 78-84.
Kaltenbach, J. A., M. A. Zacharek, et al., (2004). Neurosci Lett 355(1-2): 121-5.
Kawaguchi, Y. and Y. Kubota (1993). J Neurophysiol 70(1): 387-96.
Kelly, J. B. and H. Zhang (2002). Hear Res 168(1-2): 35-42.
Kepecs, A. and J. Lisman (2003). Network 14(1): 103-18.
Kepecs, A., X. J. Wang, et al., (2002). J Neurosci 22(20): 9053-62.
Kraus, N., T. McGee, et al., (1992). Ear Hear 13(3): 158-64.
Kraus, N., T. McGee, et al., (1994). J Neurophysiol 72(3): 1270-7.
LeDoux, J. E., A. Sakaguchi, et al., (1984). J Neurosci 4(3): 683-98.
Lee et al., J. Neurosci. 2001 Mar. 1; 21(5):1757-66.
Lever et al., J. Neurosci. 2001 Jun. 15; 21(12):4469-77.
Lisman, J. E. (1997). Trends Neurosci 20(1): 38-43.
Ma, C. L., J. B. Kelly, et al., (2002). Hear Res 168(1-2): 25-34.
Martin, W. H., J. W. Schwegler, et al., (1993). Laryngoscope 103(6): 600-4.
Massaux, A. and J. M. Edeline (2003). Exp Brain Res 153(4): 573-8.
Massaux, A., G. Dutrieux, et al., (2004). J Neurophysiol 91(5): 2117-34.
Mattia et al., Hippocampus. 1997; 7(1):48-57.
Matveev, Cerebral Cortex, Vol. 10, No. 11, 1143-1153, November 2000.
McAlonan and Brown, Neuroscientist. 2002 August; 8(4): 302-5.
McCormick, D. A. and H. R. Feeser (1990). Neuroscience 39(1): 103-13.

McCormick, D. A. and M. von Krosigk (1992). Proc Natl Acad Sci USA 89(7): 2774-8.
Miller, L. M., M. A. Escabi, et al., (2001). J Neurosci 21(20): 8136-44.
Miller, L. M., M. A. Escabi, et al., (2001). Neuron 32(1): 151-60.
Moller, A. R. (1984). Ann Otol Rhinol Laryngol 93(1 Pt 1): 39-44.
Mooney, D. M., L. Zhang, et al., (2004). Proc Natl Acad Sci USA 101(1): 320-4.
Muller, J. R., A. B. Metha, et al., (1999). Science 285(5432): 1405-8.
N. Urbain, et al., J. Neurosci., Oct. 1, 2002; 22(19): 8665-8675
Naätanen, R. (1992). Attention and brain function. Hillsdale, N.J., Lawrence Erlbaum.
Naatanen, R. (2001). Psychophysiology 38(1): 1-21.
Naatanen, R., P. Paavilainen, et al., (1993). Psychophysiology 30(5): 436-50.
Nousak, J. M., D. Deacon, et al., (1996). Brain Res Cogn Brain Res 4(4): 305-17.
Ochi, K. and J. J. Eggermont (1996). Hear Res 95(1-2): 63-76.
Ochi, K. and J. J. Eggermont (1997). Hear Res 105(1-2): 105-18.
Ohzawa, I., G. Sclar, et al., (1985). J Neurophysiol 54(3): 651-67.
Oleskevich, S. and B. Walmsley (2002). J Physiol 540(Pt 2): 447-55.
Pantev, C., H. Okamoto, et al., (2004). Eur J Neurosci 19(8): 2337-44.
Perez-Reyes, E. (2003). Physiol Rev 83(1): 117-61.
Poremba, A., D. Jones, et al., (1998). Eur J Neurosci 10(10): 3035-43.
Puel, J. L. (1995). Prog Neurobiol 47(6): 449-76.
Puel, J. L., J. Ruel, et al., (2002). Audiol Neurootol 7(1): 49-54.
Ramcharan, E. J., C. L. Cox, et al., (2000). J Neurophysiol 84(4): 1982-7.
Ritter, W., D. Deacon, et al., (1995). Ear Hear 16(1): 52-67.
Romanski, L. M. and J. E. LeDoux (1992). J Neurosci 12(11): 4501-9.
Sakurai, Y. (1990). Behav Neurosci 104(2): 253-63.
Sakurai, Y. (2002). Neuroscience 115(4): 1153-63.
Sanes, D. H., J. McGee, et al., (1998). J Neurophysiol 80(1): 209-17.
Schwarz, D. W., F. Tennigkeit, et al., (2000). Acta Otolaryngol 120(2): 251-4.
Schwindt and Crill, J. Neurophysiol. 1999 March; 81(3): 1341-54.
Sherman, S. M. (2001). Nat Neurosci 4(4): 344-6.
Sherman and Guillery, Neuron. 2002 Jan. 17; 33(2):163-75.
Sherman and Guillery, Philos Trans R Soc Lond B Biol Sci. 2002 Dec. 29; 357(1428):1695-708.
Sherman and Guillery, Philos Trans R Soc Lond B Biol Sci. 2002 Dec. 29; 357(1428):1809-21.
Sherman, S. M. (2001). Trends Neurosci 24(2): 122-6.
Steriade, M. and R. R. Llinas (1988). Physiol Rev 68(3): 649-742.
Steriade, M., D. Pare, et al., (1989). J Neurosci 9(7): 2215-29.
Steriade, Neuroscience. 2000; 101(2):243-76.
Suga, N., Y. Zhang, et al., (1997). J Neurophysiol 77(4): 2098-114.
Swadlow, H. A. and A. G. Gusev (2001). Nat Neurosci 4(4): 402-8.
Tabak, J. and P. E. Latham (2003). Neuroreport 14(11): 1445-9.
Tennigkeit, F., D. W. Schwarz, et al., (1996). J Neurophysiol 76(6): 3597-608.
Tennigkeit, F., E. Puil, et al., (1997). Acta Otolaryngol 117(2): 254-7.
Tiitinen, H., K. Alho, et al., (1993). Psychophysiology 30(5): 537-40.
Traub et al., J. Physiol. 1994 Nov. 15; 481 (Pt 1):79-95.
Ulanovsky, N., L. Las, et al., (2003). Nat Neurosci 6(4): 391-8.
van Vreeswijk, C. and D. Hansel (2001). Neural Comput 13(5): 959-92.
Wan et al., Neuroscience. 2004; 125(4):1051-60.
Webster, W. R. (1971). Electroencephalogr Clin Neurophysiol 30(4): 318-30.
Weinberger, N. M. (1998 Neurobiol Learn Mem 70(1-2): 226-51.
Weinberger, N. M. (2004). Nat Rev Neurosci 5(4): 279-90.
Weinberger, N. M. and J. S. Bakin (1998). Audiol Neurootol 3(2-3): 145-67.
Wong and Stewart, J. Physiol. 1992 November; 457:675-87.
Wu, S. H., C. L. Ma, et al., (2004). J Neurosci 24(19): 4625-34.
Zacharek, M. A., J. A. Kaltenbach, et al., (2002). Hear Res 172(1-2): 137-43.
Zhang, J. S. and J. A. Kaltenbach (1998). Neurosci Lett 250(3): 197-200.
Zhang, Y., N. Suga, et al., (1997). Nature 387(6636): 900-3.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of stimulating nerve tissue of a patient using an implantable pulse generator, the method comprising:
generating, by the implantable pulse generator, a burst stimulus that comprises a repeating pattern of a plurality of groups of pulses, wherein the burst stimulus is substantially quiescent between each adjacent group of pulses, wherein pulses within each group of pulses are repeated at a pulse rate of approximately 500 Hz and groups of pulses within the plurality of groups are repeated at approximately 40 Hz, wherein the burst stimulus is adapted to repetitively cause a group of stimulated neurons to experience a rise above a resting electrical potential to a reference potential, to be maintained at or above the reference potential for a duration of multiple pulses of a respective group of pulses, and to experience spiking from the multiple pulses of the respective group of pulses;
providing the burst stimulus from the implantable pulse generator to a medical lead; and treating chronic pain in the patient by applying the burst stimulus to afferent somatosensory fibers of the dorsal column the patient via one or several electrodes of the medical lead.

2. The method of claim 1 further comprising: controlling a number of pulses within a group of pulses of the burst stimulus according a parameter stored in the implantable pulse generator.

3. The method of claim 1 further comprising: controlling a pulse amplitude according to a parameter stored in the implantable pulse generator.

4. The method of claim 1 further comprising: controlling a pulse-to-pulse interval according to a parameter stored in the implantable pulse generator.

5. The method of claim 1 further comprising: controlling a group-to-group interval according to a parameter stored in the implantable pulse generator.

6. The method of claim 1 further comprising: controlling a number of groups within the burst stimulus according to a parameter stored in the implantable pulse generator.

7. The method of claim 1 further comprising: generating a hyperpolarizing pulse immediately before each group of pulses within the burst stimulus.

8. The method of claim 7 wherein an amplitude of the hyperpolarizing pulse is controllable by a parameter stored in the implantable pulse generator.

9. The method of claim 1 further comprising: detecting, by the implantable pulse generator, hyperactivity within neural tissue using a sensor in the implantable pulse generator, wherein the generating the burst stimulus occurs in response to the detecting.

10. The method of claim 9 wherein the sensor is coupled to one or several electrodes of the medical lead.

* * * * *